United States Patent
Stack et al.

(10) Patent No.: US 7,194,368 B2
(45) Date of Patent: Mar. 20, 2007

(54) METHOD AND APPARATUS FOR CORRECTING OUTPUT INFORMATION OF FLOW MEASUREMENT APPARATUS

(75) Inventors: Charles Paul Stack, Louisville, CO (US); Craig B. McAnally, Thornton, CO (US); Gregory Treat Lanham, Longmont, CO (US)

(73) Assignee: Micro Motion, Inc, Boulder, CO (US)

( * ) Notice: Subject to any disclaimer, the term of this patent is extended or adjusted under 35 U.S.C. 154(b) by 0 days.

(21) Appl. No.: 10/566,613

(22) PCT Filed: Aug. 29, 2003

(86) PCT No.: PCT/US03/27126

§ 371 (c)(1),
(2), (4) Date: Jan. 31, 2006

(87) PCT Pub. No.: WO2005/031285

PCT Pub. Date: Apr. 7, 2005

(65) Prior Publication Data

US 2006/0195282 A1    Aug. 31, 2006

(51) Int. Cl.
*G06F 19/00* (2006.01)

(52) U.S. Cl. .................................... 702/100
(58) Field of Classification Search ............... 702/100, 702/12, 45, 50, 114; 700/281; 73/1
See application file for complete search history.

(56) References Cited

U.S. PATENT DOCUMENTS

| | | | |
|---|---|---|---|
| 5,228,327 A | * | 7/1993 | Bruck ......................... 73/1.34 |
| 5,594,180 A | | 1/1997 | Carpenter et al. |
| 5,827,979 A | | 10/1998 | Schott et al. |
| 5,983,700 A | | 11/1999 | Yamaguchi et al. |
| 6,327,915 B1 | | 12/2001 | Van Cleve et al. |

FOREIGN PATENT DOCUMENTS

GB    2272287 A    5/1994

\* cited by examiner

*Primary Examiner*—Michael Nghiem
*Assistant Examiner*—Tung Lau
(74) *Attorney, Agent, or Firm*—The Ollila Law Group LLC

(57) ABSTRACT

A method and apparatus of correcting flow information generated by flow measurement apparatus, such as a Coriolis flowmeter. The disclosed method and apparatus corrects flow information generated during low flow and zero flow rates by blocking the application of spurious flow signals from the output of the flowmeter.

14 Claims, 14 Drawing Sheets

METHOD AND APPARATUS FOR CORRECTING OUTPUT INFORMATION OF FLOW MEASUREMENT APPARATUS

FIELD OF THE INVENTION

This invention relates to a method and apparatus for preventing flow measurement apparatus from generating an output signal representing a material flow during a zero flow state of the apparatus. More particularly this invention relates to a method and apparatus that overcomes problems of "zero drift" and causes an apparatus such as a Coriolis flowmeter to report a flow signal of "0" to a user during a "zero flow" state of the meter. This invention further relates to a method and apparatus that corrects flow information generated during a low flow state of said apparatus.

Problem

Coriolis effect mass flowmeters generate mass flow and other information for materials flowing through a conduit in the flowmeter. Exemplary Coriolis flowmeters are disclosed in U.S. Pat. No. 4,109,524 of Aug. 29, 1978, U.S. Pat. No. 4,491,025 of Jan. 1, 1985, and Re. 31,450 of Feb. 11, 1982, all to J. E. Smith et al. These flowmeters have one or more conduits of a straight or curved configuration. Each conduit configuration in a Coriolis mass flowmeter has a set of natural vibration modes, which may be of a simple bending, torsional or coupled type. Each conduit is driven to oscillate in one of these natural modes. Material flows into the flowmeter from a connected pipeline on the inlet side of the flowmeter, is directed through the conduit or conduits, and exits the flowmeter through the outlet side of the flowmeter. The natural vibration modes of the vibrating, material filled system are defined in part by the combined mass of the conduits and the contained material.

When there is no flow through the flowmeter, all points along the conduit oscillate due to an applied driver force with identical phase or a small initial fixed phase offset which can be corrected. As material begins to flow, Coriolis forces cause each point along the conduit to have a different phase. The phase on the inlet side of the conduit lags the driver, while the phase on the outlet side of the conduit leads the driver. Pickoff sensors coupled to the conduit(s) to produce sinusoidal signals representative of the motion of the conduit(s). Signals output from the pickoff sensors are processed to determine the phase difference between the pickoff sensors. The phase difference between two pickoff sensor signals is proportional to the mass flow rate of material through the conduit(s).

Coriolis mass flowmeters calculate mass flow rate from a time delay measurement where time delay arises from the Coriolis effect and is directly proportionally to the mass flow rate. For an ideal Coriolis mass flowmeter (one that is completely symmetric from its inlet to its outlet and is undamped) measuring time delay is all that is needed to accurately determine mass flow rate. However, Coriolis mass flowmeters are inevitably nonsymmetric and are subject to structural and viscous damping. As a result, under no flow conditions a small amount of time delay is present. This time delay is measured and subtracted from the time delay induced by the Coriolis effect to obtain a zero time delay.

It is a problem that the time delay of a Coriolis flowmeter at zero flow is never constant. This is termed "zero drift." The typical way of handling this zero drift problem is by using a low flow cut-off value that is an arbitrarily small portion of the flow output signal at material flow. Mass flow values below this arbitrary low flow-out-off value are assumed to be zero and a mass flow rate signal of zero is reported to the user for mass flows less than this arbitrary value. A problem arises when the time delay at zero flow drifts above the arbitrary low flow cut-off value. This can result in an erroneous flow rate output signal being reported to the user during conditions in which there is no actual material flow.

The mechanism that causes the zero flow value to drift under zero flow conditions can also be a problem during flow conditions. If the mass flow rate output signal is sufficiently large, this is a minor problem because the contribution of the time delay at zero flow is small and does not represent a significant error of the reported flow. However, for low flow rates, this arbitrarily specified zero drift value can become embedded in the total flow and be a significant source of error.

The use of a low flow cut-off value is satisfactorily as long as the conditions under which the zero drift value is captured are time invariant enough so that the time delay detected by the pickoff at zero flow remains below the low flow cut-off value. However, it is sometimes a problem that if a Coriolis flowmeter remains in a zero flow state for an extended period of time (where the period is variable depending upon the characteristics of the material), the time delay detected by the pickoff begins to drift away from zero and can result in a flow indication exceeding the low flow cut-off valve during the zero flow state of the flowmeter.

Thus, the use of the assigned low flow cut-off value to report a flow of zero is not always sufficient to prevent the reporting of a mass flow under conditions in which there is actually no material flow present. Given enough time, this zero flow drift can become greater than the low flow cut-off set point. Under this condition the flowmeter will began to report flow output signal even though there is no material flowing through the flowmeter. The traditional methods of solving this problem can cause flow measurement errors. A first traditional solution is to increase the low flow cut-off point to a higher value. This solution results in more flow measurement errors since higher low flow cut-off levels result in more true flow data being ignored by getting forced to zero. A second traditional solution is for the customer to recalibrate the flowmeter. This solution is unnecessary since the zero flow drift is not a function of the meter. It is a function of the material contained within the meter at zero flow. The recalibration of the meter will only create more errors in the true flow reading.

One of the causes of zero flow drift is the presence of two phase material and/or bubbles in the contained material. Since the driver of a Coriolis flowmeter continues to vibrate the flow tube during conditions of zero flow, a continued vibration is imparted to the contained material including the bubbles. This continued vibration during the zero flow state causes the bubbles to migrate. This migration simulates a true material flow that is detected by the pickoff with a resulting phase or time difference being detected by the pickoff. This, in turn, causes the associated meter electronics to respond to the pickoff signals and generate an output indicating a material flow. During extended no flow conditions, the migration of the bubbles can generate a phase difference between the pickoff that can far exceed the low flow cut-off point and approach a magnitude associated with a significant material flow.

Solution

The above and other problems are solved by the method and apparatus of the present invention in accordance with which problems of zero drift are solved by creating an adaptively changing set of deviation limits that track a spurious flow signal generated by the flowmeter during its zero flow state. The spurious flow signal is sampled for the duration of the zero flow state. But it is not applied to the output of the flowmeter. The operation of the flowmeter is such that it alternates between a true material flow condition and a zero flow state during which the flowmeter can generate spurious flow signals due to abnormalities (such as bubbles and the like) in the contained material even though material is not flowing through the flowmeter. It is desired that this spurious flow information not be applied to the output of the flowmeter during the zero flow state.

In accordance with a first possible embodiment of the present invention, an output signal of "zero" representing zero material flow rate is applied to the flowmeter output during the zero flow state. The spurious flow information is blocked but is analyzed to determine the end of the zero flow state at the beginning of a true material flow condition.

At the beginning of each zero flow state, this spurious flow rate signal is sampled during the zero flow state including its changes in value over the period of time the Coriolis flowmeter remains in the zero flow state. In accordance with the invention, output signal deviation limits specified by the user are defined. These deviations limits are adaptively redefined for the duration of the zero flow state. As long as each sample of the spurious flow signal remains within the adaptively changing deviation limits, the flowmeter continues to report zero material flow and no corrective action is taken. This is true even if the spurious flow rate represents a value far in excess of the user specified low cut-off value. This operation is predicated upon the fact that the spurious flow rate signal does not represent a true material flow, regardless of its value. A true material flow condition will result in a sudden increase or decrease in the output of the flowmeter that far exceeds the permissible deviation limits. In other words, a constantly changing spurious flow rate signal during a zero condition flow, regardless of its magnitude, cannot represent a true material flow as long as the signal remains between the deviation limits.

The initiation of a true material flow condition results in a change in the amplitude of the output signal that far exceeds the limits specified by the adaptively defined deviation limits. This represents the termination of a zero flow state and the initiation of a true material flow. This change in amplitude may be either a significant increase or a significant decrease from the signal amplitude generated during an extended zero flow condition. In accordance with the invention, the flowmeter terminates the sampling function of the spurious flow signal during the zero flow state and reports the magnitude of a true material flow when the termination of the zero flow state is detected.

The Coriolis flowmeter continues to report the true material flow until the material flow magnitude falls below a low flow cut off point. The meter then reverts to the zero flow state in which it again samples the spurious flow signal generated by the flowmeter. The sampling continues as the spurious flow signal gradually drifts with time and indicates a continued zero flow state. The sampling state ends when the signal suddenly changes in amplitude by an amount that exceeds the deviation limits. This change indicates the start of a true material flow. The flowmeter then again terminates its sampling function and reports the true flow rate of the flowmeter.

The above and other problems are solved by the method and apparatus of a second possible embodiment of the present invention in accordance with which problems of zero drift are solved by creating an adaptively changing set of deviation limits that track a flow signal representing the correspondence between time delay $\Delta t$ and input power. This signal is generated by the flowmeter during its zero flow state and is sampled and converted to data points for the duration of the zero flow state. The operation of the flowmeter is such that it alternates between a true material flow condition and a zero flow state during which the flowmeter can generate spurious flow information signal due to abnormalities (such as bubbles and the like) in the contained material even though material is not flowing through the flowmeter. It is desired that this spurious flow information not be applied to the output of the flowmeter during the zero flow state. An output signal of "zero" representing zero material flow rate is applied to the flowmeter output during the zero flow state. The spurious flow information is blocked but is analyzed to determine the end of the zero flow state at the beginning of a true material flow condition.

The spurious flow signal is sampled and converted into a plurality of defined data points at a rate of approximately 20 samples per second. The first few data points (approximately 20) are processed, and curve fitted to convert them to an expression representing the correlation between input power to the flowmeter and the time delay $\Delta t$ between the signals generated by the flowmeter pickoffs. The resulting expression is in the form of $$y = mx + b$$

Where
m=is the slope of the line representing the expression;
x=the time delay of each data point; and
b=the intercept of the expression on the y axis representing units of input power.

In accordance with the well known curve fitting techniques, the derived expression indicates the correlation between time delay and input power for the values of these parameters associated with the expected operating range and conditions of the zero flow state of the flowmeter. A set of deviation limits (upper and lower) are also generated that track the generated expression representing the time delay and input power parameters.

Subsequent to the generation of the derived expression, the remainder of the spurious flow signal generated during the zero flow state is sampled and used to define data points during the time interval the flowmeter remains in the zero flow state. The sampling of the spurious flow signal includes a determination of the time delay $\Delta t$ and input power associated with the data point. The sampling also includes a determination of the $\Delta t$ magnitude for the data point location. If a data point falls between the upper and lower deviation limits, processing circuitry determines that the flowmeter is still in the zero flow state and the sampling continues. If a defined data point is not between the deviation limits, the processing circuitry of the present invention determines that the flowmeter is no longer in a zero flow state and that the sampled flow signal has a magnitude indicative of a true material flow. The processing circuitry then causes the flowmeter to generate an output signal representing a true material flow.

As long as each data point remains within the adaptively changing deviation limits, the flowmeter continues to report a flow signal of zero and no further action is taken. This is true even if the flow rate for the data point represents a value far in excess of the user specified low flow cut-off value. This is predicated upon the fact that the spurious flow rate signal being sampled does not represent a true material flow, regardless of its magnitude, since a true material flow condition, as subsequently described, results in a sudden increase or decrease in the signal magnitude that far exceeds the deviation limits of the sampled zero flow state signal. In other words, a constantly changing spurious sampled flow signal during a zero flow state, regardless of its magnitude, cannot represent a true material flow as long as the sampled signal remains between the deviation limits.

The initiation of a true material flow is detected by a change in the amplitude of the sampled signal that far exceeds the adaptively defined deviation limits. This represents the termination of a zero flow state and the initiation of a true material flow. This change in amplitude of the sampled signal may be either a significant increase or decrease in the relationship of Δt to the input power during a zero flow condition. The flowmeter terminates the zero flow sampling function and reports the magnitude of a true material flow when the zero flow state ends.

The Coriolis flowmeter continues to report the magnitude of the true material flow until the material flow falls below the low flow cut off point. The meter then reverts to the zero flow state in which it again samples the flow signal detected by the pickoffs. The sampling continues while the flow signal drifts with time and indicates a continued zero flow state. The sampling ends when the signal again changes in amplitude by an amount that exceeds the deviation limits. This indicates the start of true material flow. The flowmeter then again terminates its sampling function and reports the true flow rate of the flowmeter.

In accordance with another embodiment, the same material abnormalities that are responsible for the generation of spurious signals during the zero flow state may be present in the flow information generated during conditions of low material flow. They can cause errors in the output information generated by the flowmeter during low flow conditions in the same manner as they do for the zero flow state. In accordance with this embodiment of the invention, these errors are avoided by the steps of:

deriving a first expression for the relationship between Δt and input power for the zero flow state;

deriving a second expression for the relationship between Δt and input power for a low flow state;

checking for equivalency between the two expressions; and subtracting the first expression from the second expression to obtain corrected flow information for the low flow state that is devoid of the errors due to the presence of the abnormalities in the material flow.

The flow information in the first expression is solely due to the abnormalities in the contained material. The flow information in the second expression consists of the same information that is in the first expression plus the information representing true material flow. Thus, subtracting the first expression from the second effectively cancels out the undesired information and leaves only the information that represents the true material flow.

Aspects

One aspect of the invention includes, a meter electronics for a flow measurement apparatus having a processing system for correcting flow information generated by said flow measurement apparatus; said meter electronics comprising:

instructions for directing said processing system to:

sample a signal representing flow information generated by said flow measurement apparatus during a zero flow state of said flow measurement apparatus to define a plurality of data points representing said signal;

establish deviation limits for at least one of said data points;

determine whether each sampled data point is within said deviation limits;

sample a data point within said deviation limits to define spurious flow information for said zero flow state;

sample a data point outside of said deviation limits to define information representing a true material flow of said flow measurement apparatus;

continue said sampling of said data points as long as said sampled data points are within said deviation limits;

prevent said spurious flow information from being applied as to an output of said flow measurement apparatus during the sampling of data points within deviation limits;

determine that the most recently sampled data point is outside of said deviation limits and thereby represents information for a true material flow of said flow measurement apparatus; and generate an output signal representing said true material flow information represented by said most recently sampled data point.

Preferably, said flow measurement apparatus defines a Coriolis flowmeter.

Preferably, said processing system is configured to execute the further instructions of:

specify a low flow cutoff limit representing a material flow below which said flow measurement apparatus will not generate an output signal representing a true material flow;

monitor the material flow information represented by said output signal;

determine that said monitored material flow information becomes less than the material flow represented by said low flow cutoff limit;

terminate the generation of said output signal; and resume the sampling of the said data points for said zero flow state of said flow measurement apparatus.

Preferably, said processing system is configured to execute the further instructions of:

determine that a newly sampled data point represents a material flow that is outside of said deviation limits; and generate an output signal for the true material flow represented by said newly sampled data point.

Preferably, said processing system is configured to execute the further instructions of:

establish said deviation limits by the step of establishing an upper limit and a lower limit of deviation associated with each sampled data point;

sample said data points as long as the spurious material flow information represented by said data point is between said upper deviation limit and said lower deviation limit;

determine that a newly sampled data point falls outside of said limits;

determine the true material flow information represented by said sampled data point; and generate an output signal representing said determined flow information.

Preferably, said processing system is configured to execute the further instructions of:

determine the average μ of the flow rates of the N previously sampled data points;

establish said standard deviation limits of the previous N data points by multiplying the product of the standard deviation r by a user specified number standard deviations A away from said average of the deviations; and add and subtract the product of rA with respect to μ.

Preferably, said processing system is configured to execute the further instructions of:

derive an expression to define data points characterizing the parameters of time delay Δt and input power of said flow measurement apparatus during a low flow state of said flow measurement apparatus;

derive an expression to define data points characterizing the parameters of Δt and input power of said flow measurement apparatus during a zero flow state of said flow measurement apparatus; and subtract said defined expression for said zero flow state from said expression for said low flow state to obtain an output signal for said flow measurement apparatus that is devoid of the spurious errors induced in said apparatus during said zero flow state.

Preferably, said processing system is configured to execute the further instructions of:

use a relationship between time delay Δt and input power of said flow measurement apparatus to derive an expression representing a plurality of said data points characterizing the generation of flow information by said flow measurement apparatus during said zero flow state.

Preferably, said processing system is configured to execute the further instructions of:

determine the deviation between subsequently sampled data points and said expression; and use said deviation determination to detect the end of said zero flow state.

Preferably, said processing system is configured to execute the further instructions of:

derive said expression by sampling said data points; and use "n" of said data points in a curve fitting operation to derive said expression.

Preferably, said processing system is configured to execute the further instructions of:

sample the remainder "m" of said sampled data points;

determine the deviation between each of said "m" sampled data points and said expression; and use said deviation determination to determine the operational state of said flow measurement apparatus.

Preferably, said processing system is configured to execute the further instructions of:

derive a plurality of said expressions for said zero flow state;

store said plurality of derived expressions in a memory;

define consistency information;

compare a newly derived expression with said stored expressions;

determine whether said newly derived expression is consistent with said stored expressions;

use said newly defined expression if it is determined to be consistent with said stored expressions; and preclude the use of said newly defined expression if it is determined to be inconsistent with said stored expressions.

Another aspect of the invention comprises a meter electronics for a flow measurement apparatus having a processing system for correcting flow information generated by said flow measurement apparatus; said meter electronics comprising:

instructions for directing said processing system to:

derive an expression to define data points for a signal characterizing the parameters of time delay at and input power of said flow measurement apparatus during a zero flow state of said flow measurement apparatus;

derive an expression to define data points characterizing the parameters of time delay Δt and input power of said flow measurement apparatus during a low flow state of said flow measurement apparatus;

subtract said expression for a zero flow state of said flow measurement apparatus from said expression for said low flow state to obtain an output signal devoid of the errors induced during said zero flow state.

Another aspect of the invention comprises a method of operating a flow measurement apparatus for correcting flow information generated by said flow measurement apparatus, said method comprising the steps of:

sampling a signal representing flow information generated by said flow measurement apparatus during a zero flow state of said flow measurement apparatus to define a plurality of data points representing said signal;

establishing deviation limits for at least some of said data points;

determining whether each sampled data point is within said deviation limits;

sampling a data point within said deviation limits to define spurious flow information for said zero flow state;

sampling a data point outside of said deviation limits to define information representing a true material flow of said flow measurement apparatus;

continuing said sampling of said data points as long as said sampled data points are within said deviation limits;

preventing said spurious flow information from being applied as to an output of said flow measurement apparatus during the sampling of data points within deviation limits;

determining that the most recently sampled data point is outside of said deviation limits and thereby represents information for a true material flow of said flow measurement apparatus; and generating an output signal representing said true material flow information represented by said most recently sampled data point.

DESCRIPTION OF THE DRAWINGS

The above and other objects and features of the invention can be better understood from a reading of the following detailed description thereof taken in conjunction with the drawings in which.

DETAILED DESCRIPTION

Figure 1:
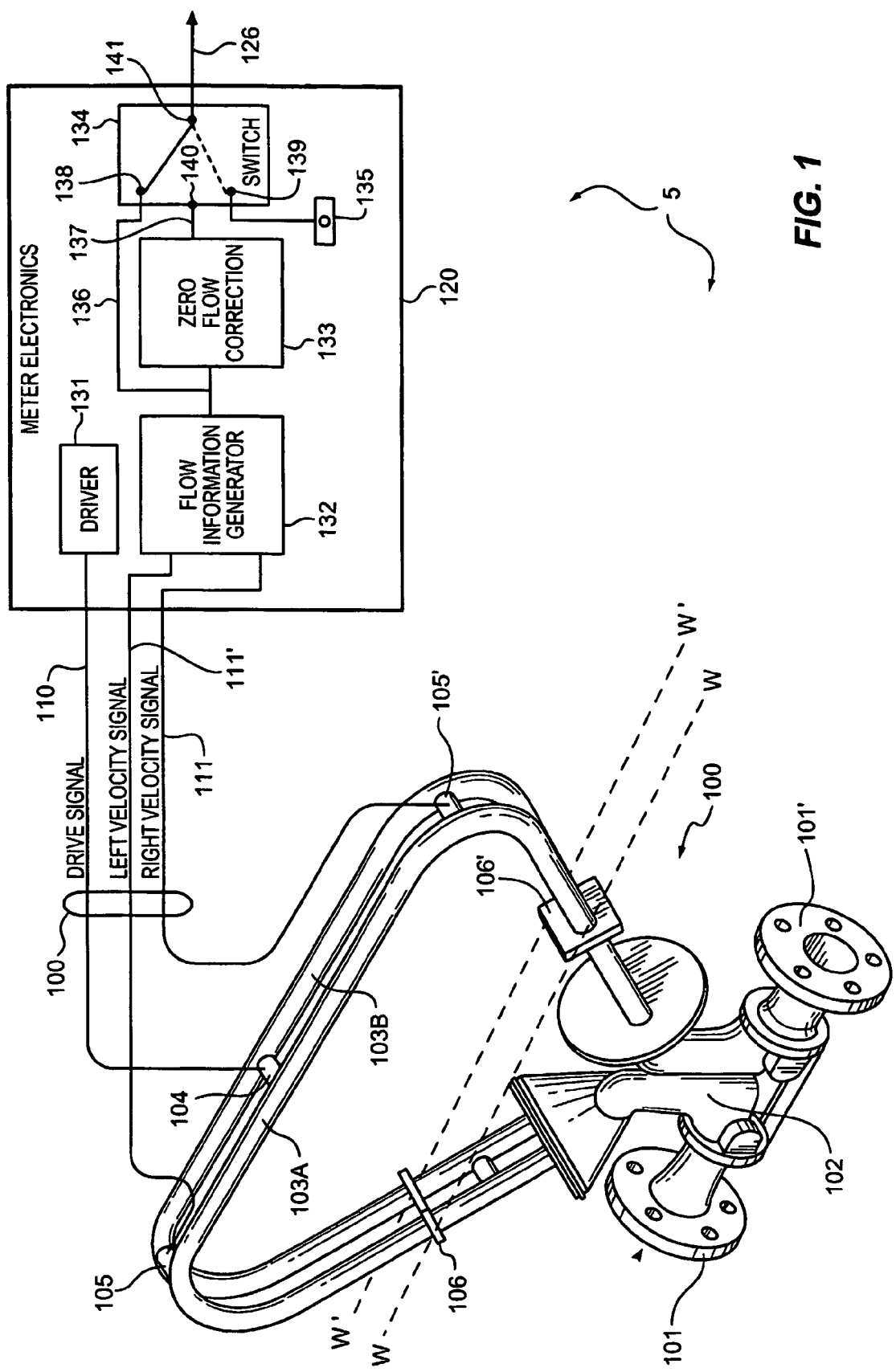
FIG. 1 illustrates a Coriolis flowmeter including meter electronics that embody the invention.

Coriolis Flowmeter in General—FIG. 1

FIG. 1 shows a Coriolis flowmeter 5 comprising a meter assembly 100 and meter electronics 120. Element 120 is connected to meter assembly 100 via leads 100 to provide density, mass flow rate, volume flow rate, temperature, totalized mass flow, and enhanced density over path 126. A Coriolis flowmeter structure is described although it should be apparent to those skilled in the art that the present invention could be practiced in conjunction with any flow measurement apparatus having a vibrating conduit to measure properties of material. A second example of such an apparatus is a vibrating tube densitometer which does not have the measurement capability provided by a Coriolis mass flowmeter.

Flowmeter assembly 100 includes a pair of flanges 101 and 101', manifold 102 and conduits 103A and 103B. Driver 104 and pickoff sensors 105 and 105' are connected to conduits 103A–B. Brace bars 106 and 106' serve to define the axis W and W' about which each conduit oscillates.

When flowmeter 100 is inserted into a pipeline system (not shown) which carries the process material that is being measured, material enters flowmeter assembly 100 through flange 101, passes through manifold 102 where the material is directed to enter conduits 103A and 103B, flows through conduits 103A and 103B and back into manifold 102 from where it exits flowmeter assembly 10 through flange 101'.

Conduits 103A and 103B are selected and appropriately mounted to the manifold 102 so as to have substantially the same mass distribution, moments of inertia and elastic modules about bending axes W—W and W'—W', respectively. The conduits extend outwardly from the manifold in an essentially parallel fashion.

Conduits 103A–103B are driven by driver 104 in opposite directions about their respective bending axes W and W' and at what is termed the first out of phase bending mode of the flowmeter. Driver 104 may comprise any one of many well known arrangements, such as a magnet mounted to conduit 103A and an opposing coil mounted to conduit 103B and through which an alternating current is passed for vibrating both conduits. A suitable drive signal is applied by meter electronics 20, via lead 110, to driver 104.

Meter electronics 120 receives the left and right velocity signals appearing on leads 111 and 111', respectively. Meter electronics 120 produces the drive signal appearing on lead 110 and causing driver 104 to vibrate tubes 103A and 103B. Meter electronics 120 processes the left and right velocity signals to compute the mass flow rate and the density of the material passing through flowmeter assembly 100. Meter electronics 120 of FIG. 1 contains a driver 131, a flow information generator 132, zero flow correction element 133 and switch 134.

Driver 131 generates the signals that are applied over path 110 driver 104 to drive flow tubes 103A and 103B in phase opposition. Flow information generator receives signals over paths 111 and 111' generated by pickoff 105 and 105'. These signals represent the Coriolis deflections that are induced in flow tubes 103A and 103B as they vibrate with material flow. These signals represent a time or a phase difference whose amplitude is proportional to the material flow within Coriolis flowmeter 100. Flow information generator 132 receives these pickoff signals and generates information pertaining to the material flow. This information may include mass flow rates and material density. The generated flow information is applied via path 136 to the input of the flow correction element 133 as well as to the upper input terminal 138 of switch 134. The flow information on path 136 that is applied to the input of the zero flow correction element 133 includes the signals 201, 301, and 401 shown on FIGS. 2, 3, and 4 respectively. The flow information on paths 201, 301, and 401 is indicative of the flow output information generated by the pickoffs. As subsequently described in detail, this signal on paths 201, 301, and 401 are sampled repeatedly to prevent the application of erroneous zero flow output information on path 126 of FIG. 1 during the zero flow state of the flowmeter.

The position of switch 134 is controlled by the signals applied by the zero flow correction element 133 over path 137 to the control input 140 of switch 134. Switch 134 is in its upper position as shown on FIG. 1 when the flowmeter is in a material flow state. At that time, the output of the flow information generator is applied over path 136 to the upper input 138 of switch 134 which is then connected by the movable element of the switch to output terminal 141 and output path 126. During this state, the signal on output path 126 represents the material flow information outputted by flow information generator 133 when there is a material flow through flowmeter 100.

The zero flow correction element 133 and switch 134 together prevent the application of erroneous output signals to path 126 where there is zero material flow through the meter. As subsequently described, during this state the zero flow correction element 133 causes an output signal of zero representing a zero flow state to be applied to output path 126. This is accomplished when the zero flow correction element 133 applies a signal over path 137 to control terminal 140 to position switch 134 it to its lower position shown by the dotted lines connecting terminals 139 and 141.

This time, zero generator 135 applies a signal of zero amplitude to terminal 139 which is extended over the movable switch contact to terminal 141 and from there to output path 126. Switch 134 remains in this position and causes a signal of zero amplitude to be applied to path 126 so long as the zero flow correction element 133 determines that flowmeter 100 is in a zero flow state.

Detailed Description of a First Possible Preferred Embodiment—FIGS. 2–5

Figure 2:
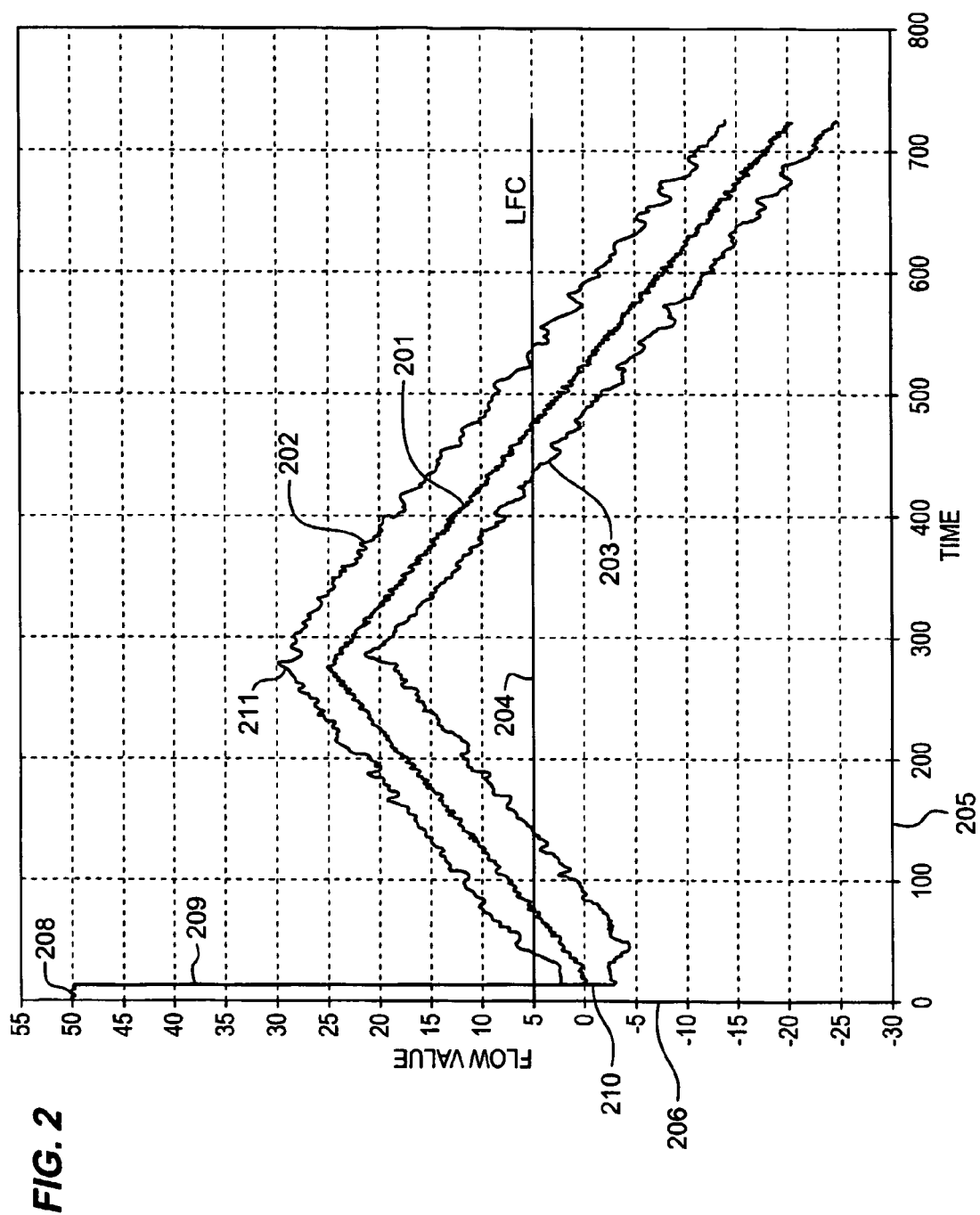
FIG. 2 is a graph illustrating the spurious flow rate signal together with assigned values of deviations for an extended zero drift state of the flowmeter.

Description of FIG. 2

FIG. 2 is a graph showing the spurious flow rate signal 201 of a flowmeter during a zero flow state. Also shown on FIG. 2 is an upper deviation limit 202 and a lower deviation limit 203. The process by which these deviation limits are generated is subsequently described.

The horizontal axis of FIG. 2 represents units of time. These units may be seconds, minutes, hours, or even days. The vertical axis represents the units of flow value. The zero point on the vertical axis represents the desired output for a zero flow state of the flowmeter. The horizontal dark line 204 represents a low flow cut-off value of 5 that is arbitrarily assigned by the user. The meter operation is such that any flow magnitude below line 204 will not be reported to a user and will be assumed to represent a zero flow state.

The output of the flowmeter on FIG. 2 begins prior to location 208 at about time 10 where the true flow is 50 flow units. This true flow state ends at location 208 in which the flow stops and falls downward on line 209 to location 210 where the flow drops to zero. The zero flow state of the flowmeter begins at location 210 and the flowmeter then generates a spurious flow signal on line 201 whose magnitude represents the signals generated by pickoffs 105 and 105' during the zero flow state portrayed on FIG. 2. As can be seen, line 201 inclines upward until about time 280 where it reaches its apex at 211. Following apex 211, line 201 declines until about time 720 where the graph of FIG. 2 terminates.

This upwards and downwards drift of line 201 represents the signals generated by the flowmeter pickoffs 105 and 105' and applied to meter electronics during the zero flow state portrayed by FIG. 2. During this time driver 104 continues to vibrate the flow tubes and agitate the contained material. As mentioned, this material may include bubbles and this agitation causes the bubbles to migrate past the pickoffs and generate phase difference signals. These phase difference signals are applied to meter electronics 120 whose element 132 generates a spurious flow rate represented by the detected phase difference. However, this spurious flow rate signal is not applied to output 126 of meter electronics 120. This random migration of bubbles generates the spurious flow rates portrayed by line 201 on FIG. 2. This spurious flow rate can vary randomly in either direction.

The upward slope of the lefthand portion of line 201 represents a spurious flow rate of increasing magnitude up to the apex 211 where it begins to decrease at time 280 and continues to decrease until the termination of the graph at time 720. The negative slope of the right hand portion of line 201 indicates a decreasing spurious flow magnitude until it crosses the zero axis at about time 480. To the right of this point, the continued decrease of line 201 indicates that the bubbles have reversed direction and are generating a output signal representing a reverse spurious flow through flowmeter 100.

The graph of FIG. 2 portrays the spurious flow rate signal 201 and its associated deviation limits 202 and 203 for the duration of the zero flow state represented by FIG. 2. Line 202 represents an upper deviation limit and line 203 represents a lower deviation limit. The flowmeter and meter electronics 120 cause the flowmeter to remain in the zero flow sampling state so long as the value of signal 201 does not exceed the deviation limits represented by lines 202 and 203 for the time beginning at location 208.

It is next described, how the flowmeter and meter electronics 120 terminate its zero flow state whenever signal 201 on FIG. 2 assumes a value that exceeds the upper limit 202 or is less than the lower limit 203.

Figure 3:
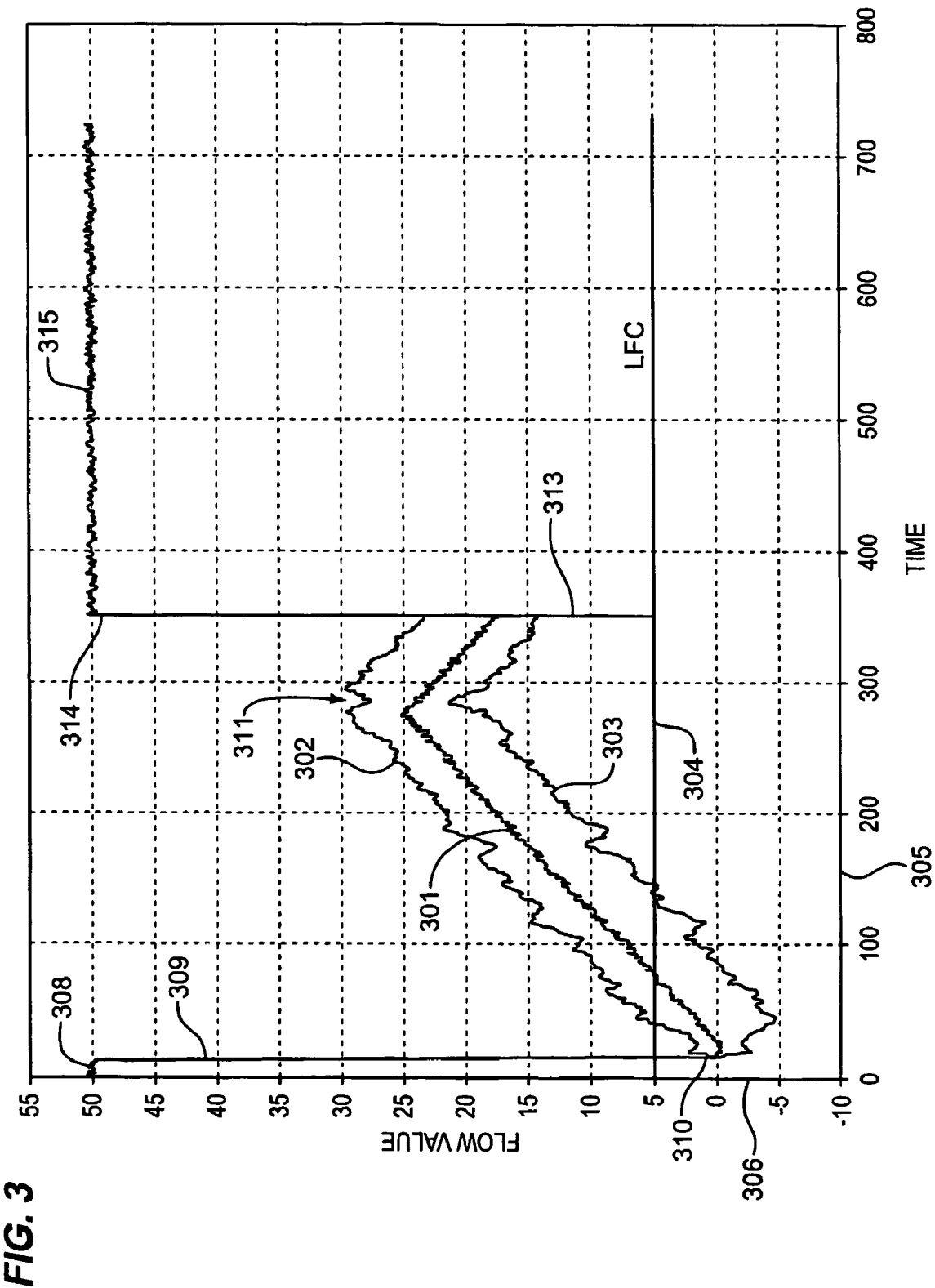
FIG. 3 is a graph that shows an output signal for a brief true flow state that is terminated and followed by a zero flow condition which is terminated by a true flow condition.

Description of FIG. 3

FIG. 3 illustrates the operation of the flowmeter embodying the present invention for a condition in which the-zero flow state is terminated and replaced by a true material flow. The graph of FIG. 3 begins with a true material flow of 50 that ends at location 308 where the output signal transitions downward along vertical line 309 to location 310. Location 310 begins a zero flow state which extends upwardly along line 301 to an apex at 311 following which it declines to location 313 where signal 301 increases dramatically to location 314 to 50 flow units. Location 313 terminates the zero flow sampling state of the flowmeter. Beginning at location 314 the flowmeter reports a true flow output of 50 units on line 315 for the duration of the time represented by the graph of FIG. 3.

In a manner similar to that described for line 201 on FIG. 2, line 301 on FIG. 3 represents the spurious flow rate of the flowmeter during the zero flow state. Lines 302 and 303 represent the deviation limits of output flow rate 301.

Figure 4:
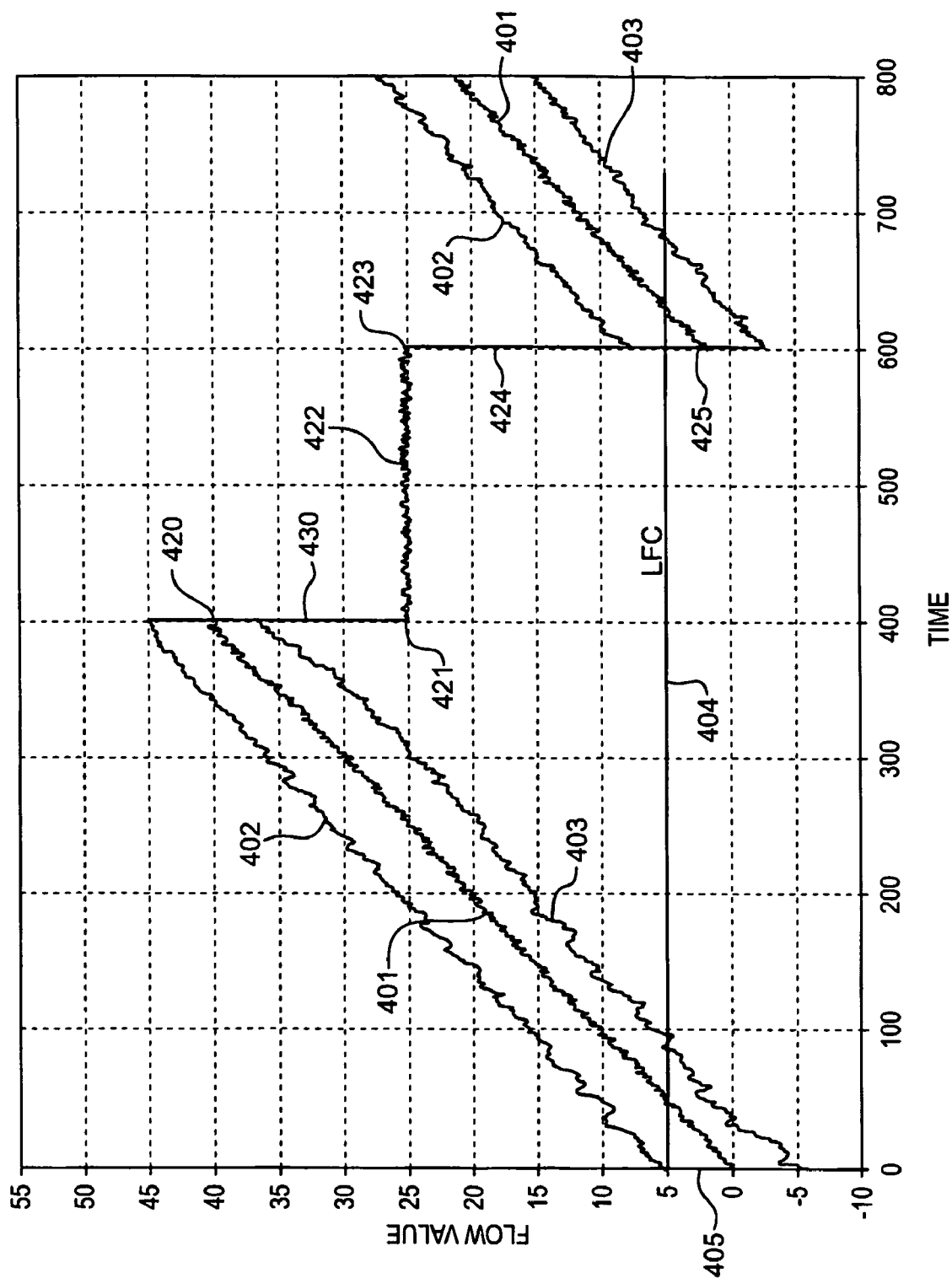
FIG. 4 is a graph showing the spurious flow rate signal of a flowmeter during an extended zero flow state together with associated deviation limits. The zero flow state is terminated by a true flow state which is terminated by a zero flow state during which the output is again monitored.

Description of FIG. 4

The graph of FIG. 4 portrays a zero flow state that begins at time zero at location 405 and terminates at location 420 when the spurious flow rate 401 decreases suddenly to location 421 along vertical line 430. Following location 421, the flowmeter reports a true material flow of approximately 25 flow units until location 423 where the flow stops and falls below the low flow cut-off value of 5 at location 425 and time 600. This begins another zero flow sampling state during which the present invention prevents the generation of erroneous output signals to path 126. As before, line 401 represents the spurious flow rate of the flowmeter during the zero flow state. Line 401 is surrounded by line 402 representing the upper deviation limit and line 403 representing the lower deviation limit.

Figure 5:
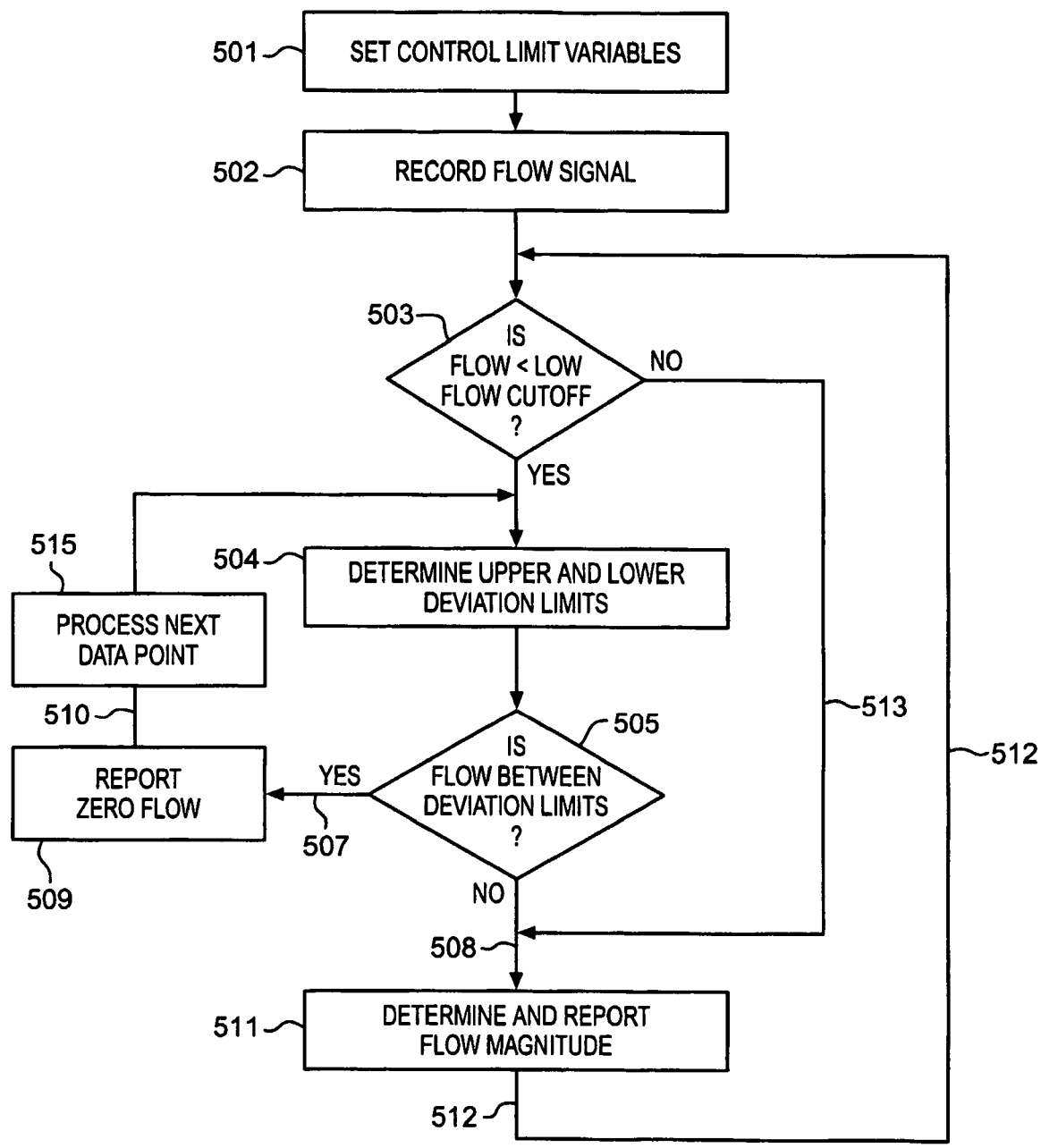
FIG. 5 is a block diagram illustrating the process steps of the present invention.

Description of FIG. 5

As mentioned, the method and apparatus of the present invention prevents the generation of erroneous flowmeter output signals to path 126 during a zero flow state by creating adaptively changing deviation limits that track the spurious flow rate of the flowmeter during the zero flow state. As long as the spurious flow rate signal 201, 301, 401 remains between the deviation limits 202,203, 302, 303 402m 403, the flowmeter reports a zero flow output signal to the user on path 126. This is accomplished by zero flow correction element 133 which incorporates a "zero-flow trending filter" that performs the steps shown on FIG. 5.

Step 501 sets the control limit variables for the system. This includes the time represented by the horizontal axis of FIGS. 2, 3, and 4. Such units could be seconds, minutes, hours, or days. It also includes the values assigned to the flow magnitude representing the vertical lines of FIGS. 2, 3, and 4. The low flow cut off value is also set to an arbitrary value, such as 5, by step 501. Step 502 records the magnitude of the flow signal applied to output path 126 by meter electronics 120 on FIG. 1. This could be the magnitude of material flow 208 and 308 on FIGS. 2 and 3 respectfully. Step 503 compares the magnitude of the material flow on path 126 to determine whether or not it is less than the low flow cut off value shown on lines 204 and 304 of FIGS. 2 and 3 respectfully. If the material flow exceeds the low flow cut off, the operation continues and signals are applied by element 503 over path 513 to element 511 which continues to report the true flow magnitude and apply an output on path 512 back to the input of element 503. The operation continues in this loop so long as the monitored flow on path 126 exceeds the low flow cut off value.

If element 503 determines that the material flow is less than the low flow cut off, a "yes" signal is sent to element 504 which assigns upper and lower deviation limits represented by lines 202 and 203 on FIG. 2 and 302 and 303 on FIG. 3 and 402 and 403 on FIG. 4.

Step 505 determines whether the spurious zero flow state signal 201, 301, 401 is between the deviation limits specified in step 504. If the answer of step 505 is "yes," a "yes" signal is applied to step 509 to cause the flowmeter and zero flow correction element 133 of meter electronics 120 of FIG. 1 to apply a signal of "0" to a user over path 126. The output of step 509 is applied to step 515 which causes the next data point to be processed and applied to element 503. Element 515 applies a signal to element 504 which processes the next data point.

The flowmeter of FIG. 1 remains in this loop condition as long as the spurious flow rate signal 201, 301, 401 remains between the deviation limits. This zero flow condition terminates when step 505 determines that the material flow is not between the deviation limits and applies a "no" signal over path 508 to step 511 which determines that the flowmeter is no longer in a zero flow state and reports the magnitude of the true material flow over path 126 on FIG. 1 to the user.

The upper and lower deviation limits of FIGS. 2, 3, 4 are calculated as follows:

$$\mu l = \mu + \sigma \times A$$

$$ll = \mu - \sigma \times A$$

Where:
μl and ll=the upper and lower deviation limits respectively.
μ=the average of the previous N samples of the fluid signal.
σ=the standard deviation of the previous N samples.
A =the number of standard deviations away from the average the limits are desired to be by the user.

This algorithm updates the deviation limits once every N samples of the spurious flow signal. This duration of N samples is user defined and may represent a duration of seconds, minutes or days. With this algorithm, the flowmeter begins the process of FIG. 5 when the flowmeter output 126 drops below the low flow cut-off point. Once the sampling process is enabled, the flowmeter continues to report zero flow to the user until there is a step change in material flow that forces the currently sampled data above or below the deviation limits. When such a step change occurs, the zero-flow-trend filter the present invention will not turn on again until the material flow rate drops below the low flow cut-off level of 5.

Description of a Second Possible Preferred Embodiment FIGS. 6–14

Figure 6:
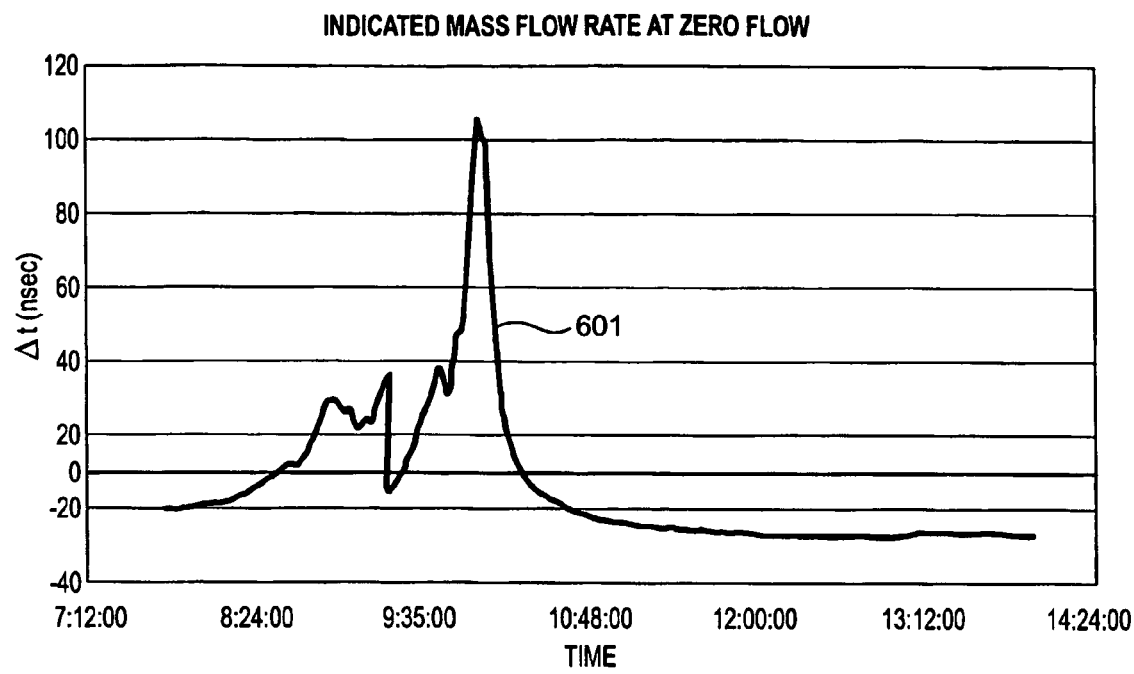
FIG. 6 is a graph illustrating the spurious zero drift time delay Δt signal generated during a zero flow state of the flowmeter.

Description of FIG. 6

FIG. 6 is a graph showing the time delay between the time delay Δt signals of pickoffs 105 and 105' during a test of a Coriolis flowmeter filled with water under conditions of zero flow. The horizontal axis represents the times at which the data is recorded. The vertical axis represents the time delay generated by the pickoffs during the test. It can be observed that the time delay 601 changes significantly with time even though there is an absence of material flow. It should also be noted that if the value of the low flow cutoff was set to 5, that there would be times during this test when the sensor of the flowmeter would indicate a material flow even though there is not actual flow.

Figure 7:
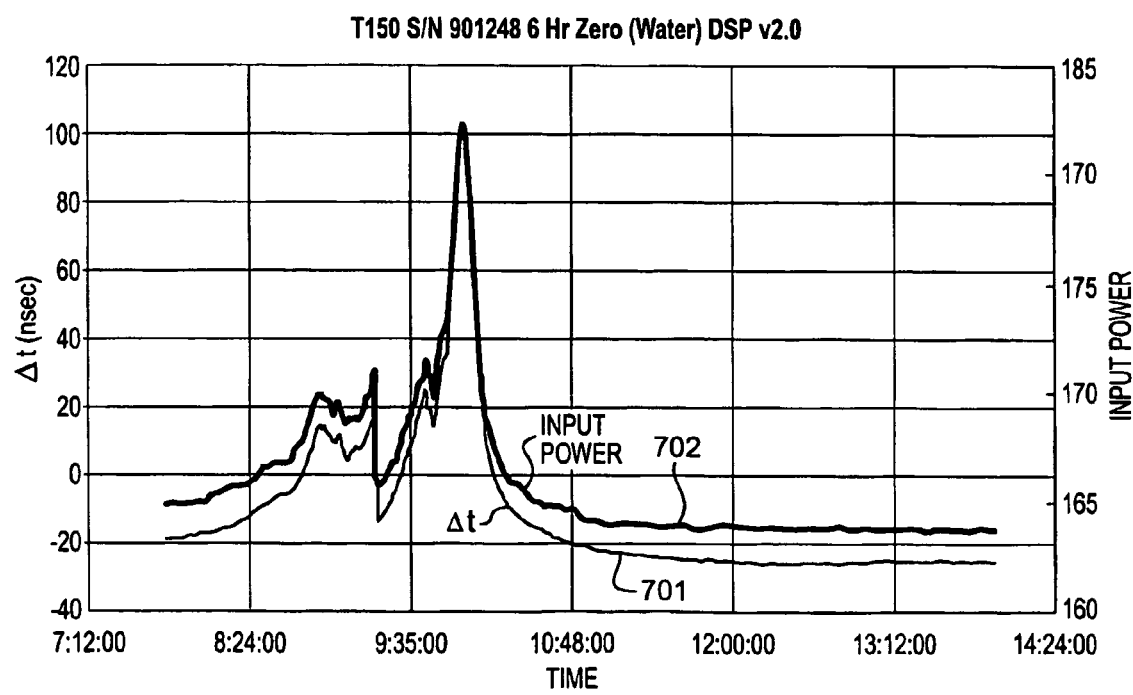
FIG. 7 is a graph that shows the correspondence between the zero drift time delay Δt and input power during a zero drift flow state of a Coriolis flowmeter.

Description of FIG. 7

FIG. 7 is a graph showing the relationship between the input power 702 and time delay 701 recorded during the test of FIG. 6. The first thing to note is that both of these variables look similar. This indicates that there is strong correlation between the input power variable and the time delay variable.

Figure 8:
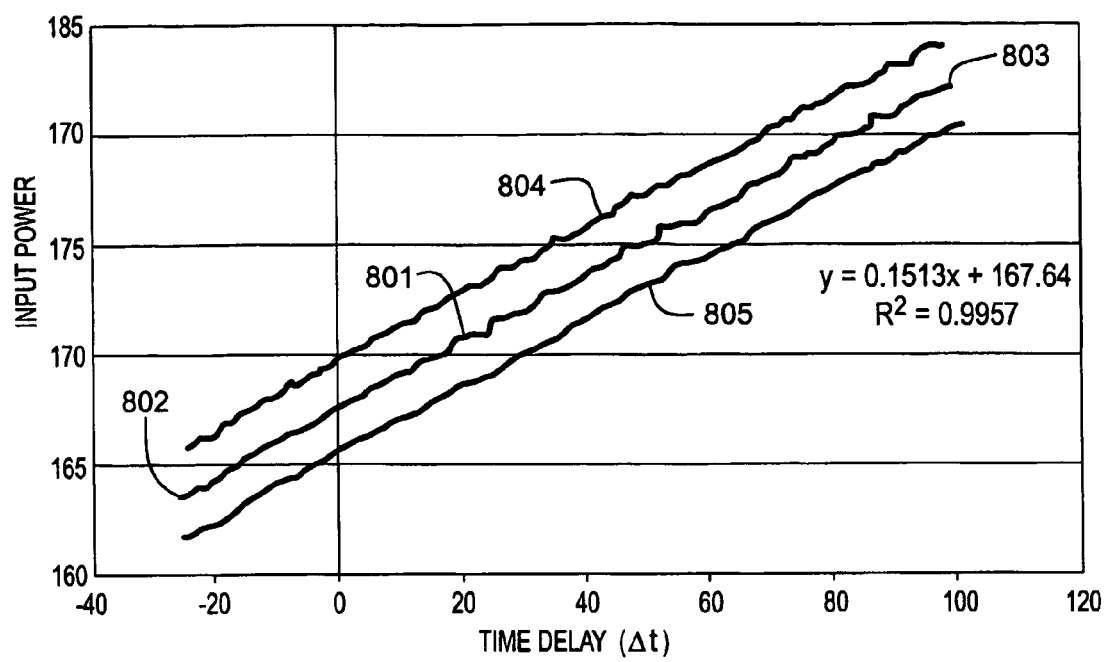
FIG. 8 is a graph showing how the samples of the time delay Δt signal of a flowmeter during a zero flow state can be expressed as an algebraic expression using curve fitting techniques to express the correspondence between input power and time delay Δt detected by the pickoffs.

Description of FIG. 8

FIG. 8 represents the data of FIG. 6 after it is sampled and curve fitted to derive the expression shown on FIG. 8 using well known curve fitting techniques such as those provided by the Excel software, a product of Microsoft.

The derived expression is $$y = +1513x + 167.64$$

Where:

$$r^2 = 0.9957$$

The slope of 0.1513 is the inclination of line 801. The term 167.64 represents the intercept on the y axis which is the input power at a time delay Δt of zero.

The fact that line 801 is essentially straight and has a constant slope from its beginning at 802 to its end at 809 supports the observation that there is a strong correlation between time delay (Δt) and input power. Also, in accordance with well known curve fitting techniques, the fact that the $r^2$ square term on FIG. 8 has a value close to "1" indicates that the variation in input power is related to the variation time delay Δt or vice versa. As a result of this correlation, the input power variables of FIG. 8 can be used as an indicator as to whether the time delay Δt obtained from pickoffs 105 and 105' during a zero flow state is caused by zero flow or changes in damping of the flowmeter or material impurities such as bubbles. If there is a high correlation between the two variables (Δt and power) the Δt signal represents changes in damping for a zero flow state. If there is low correlation between the two signals, the Δt represents material flow.

Figure 9:
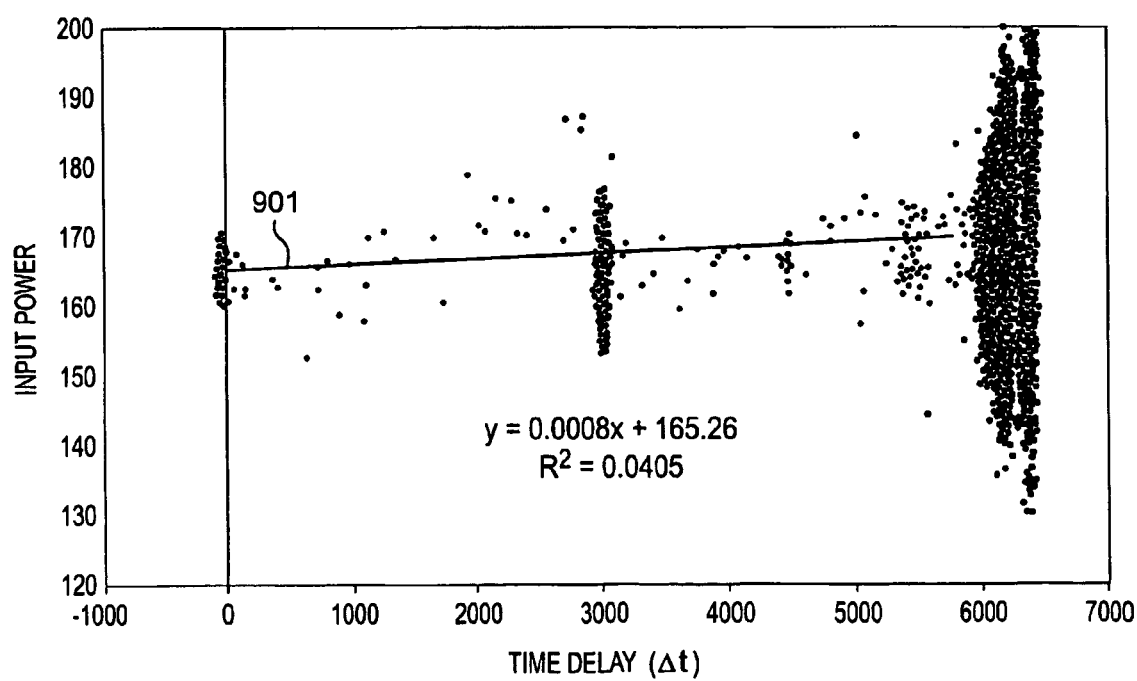
FIG. 9 shows the lack of correspondence between drive gain and time delay Δt during a material flow state.

Description of FIG. 9

FIG. 9 shows the data generated by the same flowmeter as FIG. 8 under conditions of material flow. The derived expression generated by the Excel curve fitting techniques for the data of FIG. 8 is y=0.0008x+165.26 where $r^2=0.0405$.

The expression for equations of this type is y=mx+b

Where:
m=equals the slope of line 901 and
b=intercept of line 901 on the y axis

The term 0.0008 represents the near horizontal slope of line 501 and that its y intercept is 165.26. The low value of the $r^2$ term (0.0405) indicates a very low correspondence between the time delay Δt variable and the input power variable.

In FIG. 9, the $r^2$ term of 0.0405 indicates that there is no meaningful correlation between the time delay Δt and the input power.

FIGS. 8 and 9 show that at low flows, the measured flow rate can be unstable but when the flow rate increases for the same material, the measured flow rate becomes stable. This phenomenon can be attributed to changes in damping being more prevalent at zero flow or low flow than under normal flow conditions and thereby causing zero drift errors.

Figure 10:
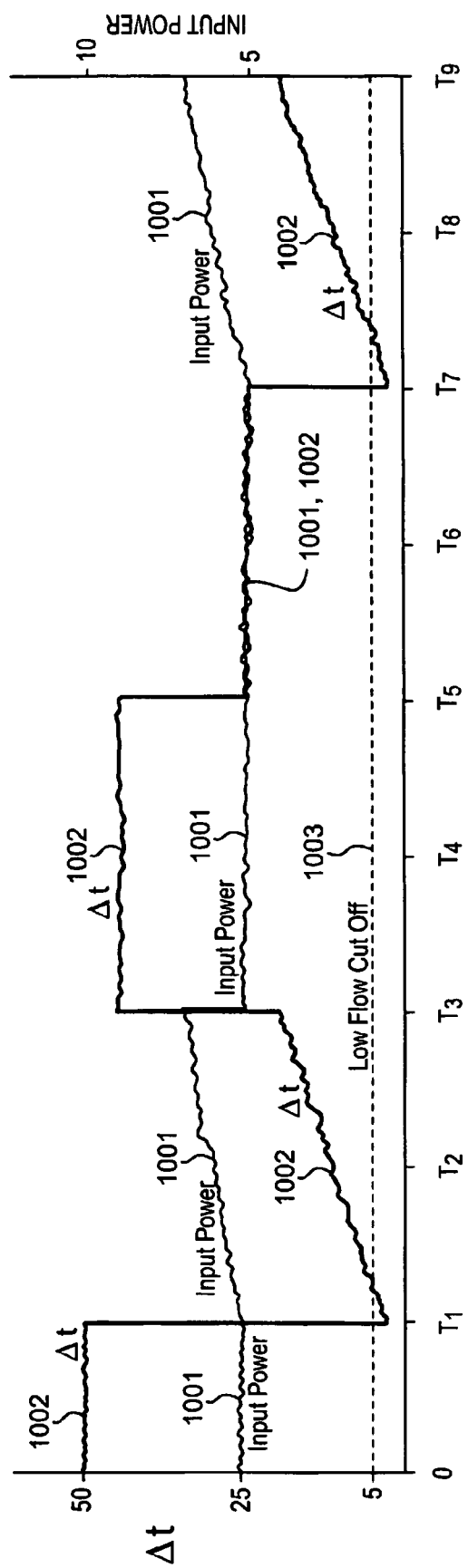
FIG. 10 is a graph representing an operation of the invention.

Description of FIG. 10

FIG. 10 illustrates the variation in time delay $\Delta t$ with respect to time for the true material flow state of the second embodiment as well for the zero flow state of the second embodiment. The left y axis on FIG. 10 represents variations in time delay $\Delta t$. The horizontal axis represents time intervals from 0 through $t_9$. On FIG. 10 a true flow state exits from time 0 to time t1. The material flow 1002 is then 50 units of $\Delta t$. This flow terminates at time $t_1$ where it falls below low flow cut-off 1003 having a value of 5. The system transitions to the zero flow state at time $t_1$ and remains there through the beginning of time $t_3$. During this interval of $t_1$ through $t_3$ the $\Delta t$ gradually increases to a value of approximately 20. At time $t_3$, the zero flow state ends and a true material flow of 50 $\Delta t$ units begins at $t_3$ and terminates at time $t_5$. At time $t_5$ the true material flow decreases from 50 to 25 and remains at 25 until time $t_7$ when the true material flow terminates and falls below the low flow cut-off 1003. From time $t_7$ through time $t_9$ the system reverts back to the zero flow state during which the time delay $\Delta t$ 1002 increases from time $t_7$ until time to.

It will be recalled from an understanding of FIG. 7 that the input power 702 deviates in the same manner as does $\Delta t$ 701 during a state of material flow. This correspondence is also shown on FIG. 8 where line 801 representing the derived expression shows that both time delay $\Delta t$ are represented by a correspondence that is essentially linear. This correspondence is represented by the derived expression which expresses the relationship between input power and $\Delta t$ for the zero flow state. It will also be recalled that for a state of true material flow that, as shown on FIG. 9, there is no correspondence between time $\Delta t$ and input power. In other words, increases and decreases in time delay $\Delta t$ have no meaningful relationship to variation in input power during material flows.

FIG. 10 validates the relationships shown between input power and $\Delta t$ for the zero flow state and the material flow state of FIGS. 8 and 9. Thus, FIG. 10 shows that the input power 1001 remains constant from time interval $t_0$ through $t_1$ when line 1002 representing $\Delta t$ remains at a constant level of 50. This corroborates the relationship shown on FIG. 9.

FIG. 10 also shows that the input power 1001 increases with a increase in $\Delta t$ from time $t_1$ to $t_3$. This corresponds to the relationship shown in FIG. 8. FIG. 10 also shows that the input power 1001 remains constant as the true material flow changes from a $\Delta t$ of 50 at time $t_5$ and falls to a $\Delta t$ of 25 where it remains until time $t_7$. During the time interval $t_3$ through $t_7$ input power 1001 remains constant with changing values of $\Delta t$ 1002. At time $t_7$ the material flow decreases below the low flow cut-off value and the system which is to the zero flow state and remains there from time $t_7$ through time $t_9$. During this zero flow interval, $\Delta t$ 1002 increases along with an increase in input power 1001.

In summary of FIG. 10, it can be seen that the input power 1001 remains essentially constant during periods of material flow even though the $\Delta t$ value of the material flow changes. FIG. 10 also shows that the input power 1001 increases along with increases in the flow $\Delta t$ during the zero flow state portrayed by time interval $t_1$ through $t_3$ and $t_7$ through time $t_9$.

Figure 11:
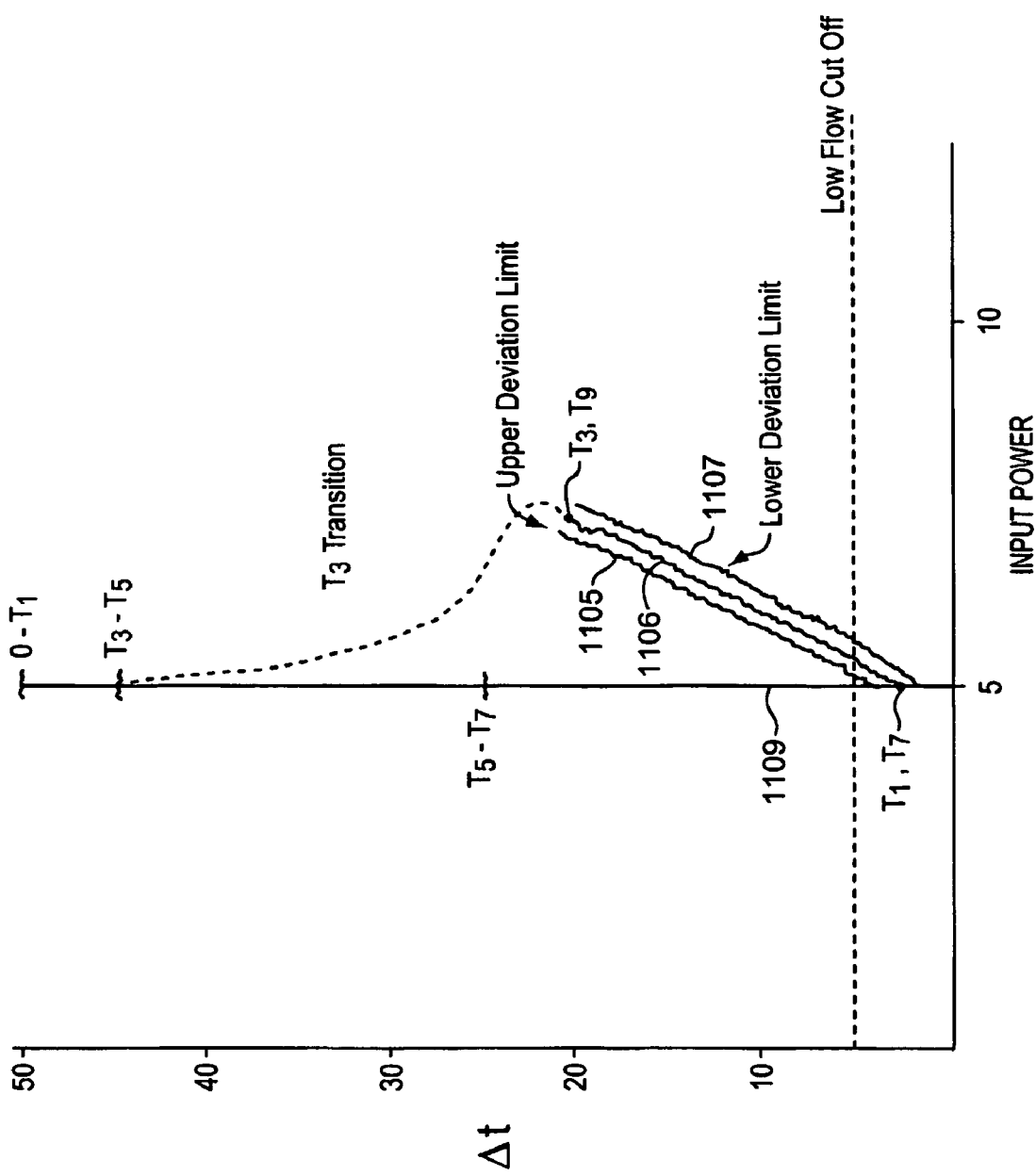
FIG. 11 is a state diagram illustrating the operation of the invention.

Description of FIG. 11

FIG. 11 is a state diagram illustrating further details of the system operation portrayed on FIG. 10. The vertical axis on FIG. 11 portrays the time delay $\Delta t$; the horizontal axis represents units of input power. The state of the system during time interval 0 through $t_1$ is shown on FIG. 11 as having a $\Delta t$ of 50 and an input power of 5. The parameters of input power and $\Delta t$ are constant during this time interval as shown at the top of vertical line for input power 5. The minor variations in these parameters during this time interval as shown as having small variations due to variations in measured input power and measured $\Delta t$. As shown on FIG. 10, the true flow state ends at time $t_1$, when the flow falls below the low flow cut-off value of 5. The zero flow state then begins.

Diagonal line 1106 corresponds to line 801 of FIG. 8 and shows as increase in both the input power and $\Delta t$ during the zero flow state. This zero flow state begins as shown on FIG. 10 at time $t_1$ and lasts through time $t_3$. The zero flow state also begins at the time of $t_7$ and ends at time $t_9$. Accordingly, on FIG. 11 the line 1106 its lower extremity designated at $t_1$ and $t_7$ corresponding to the beginning at the time intervals in which the system is in its zero flow state. Line 1106 also has its upper extremity designated as time $t_3$ and $t_9$ corresponding to the time interval designations in which the zero flow state ends as shown on FIG. 10. Lines 1105 and 1107 opposite sides of line 1106 are the upper and lower deviation limits respectively corresponding to deviation limits 804 and 805 on FIG. 8.

Thus, the time interval $t_1$ through $t_3$ for the zero flow shown on FIG. 10 is portrayed on FIG. 11 by line 1106 and its adjacent deviation limits 1105 and 1107. This zero flow state interval terminates at time $t_3$ and the system transitions on FIG. 11 up to along the dotted line the location for interval $t_3$ through $t_5$ on line 1109 representing a true material flow having a value of 45 $\Delta t$ units and an input power of 5 as shown for line 1001 on FIG. 10. This system remains in this state until time $t_5$ where the true material flow transitions down to 25 $\Delta t$ units and remains there through time $t_7$. This transition is also shown on FIG. 11 and is located on the vertical line 1109 representing an input power of 5 units.

The system transitions from the state of true material flow when the true flow falls below the low flow cut-off of 5 at time $t_7$. The system then reverts to the zero flow state in which both the $\Delta t$ 1002 and the power input 1001 increase in a corresponding manner as shown on FIG. 10. This is once again portrayed by the line 1106 which begins at time $t_7$ and ends time $t_9$.

FIG. 11 clearly shows that the input power of line 1109 remains at a constant value of 5 power units during the time intervals in which the system is in a state of true material flow. These time intervals are clearly shown on FIG. 11 are $t_0$–$t_1$, $t_3$–$t_5$ and $t_5$–$t_7$. FIG. 11 also shows that the input power changes with changes in $\Delta t$ during the time intervals in which the system is in the zero flow state. This is portrayed on FIG. 11 by the line 1106 which increases in both power and $\Delta t$ from time $t_1$ through time $t_3$ as well as from time $t_7$ through time $t_9$.

Figure 12:
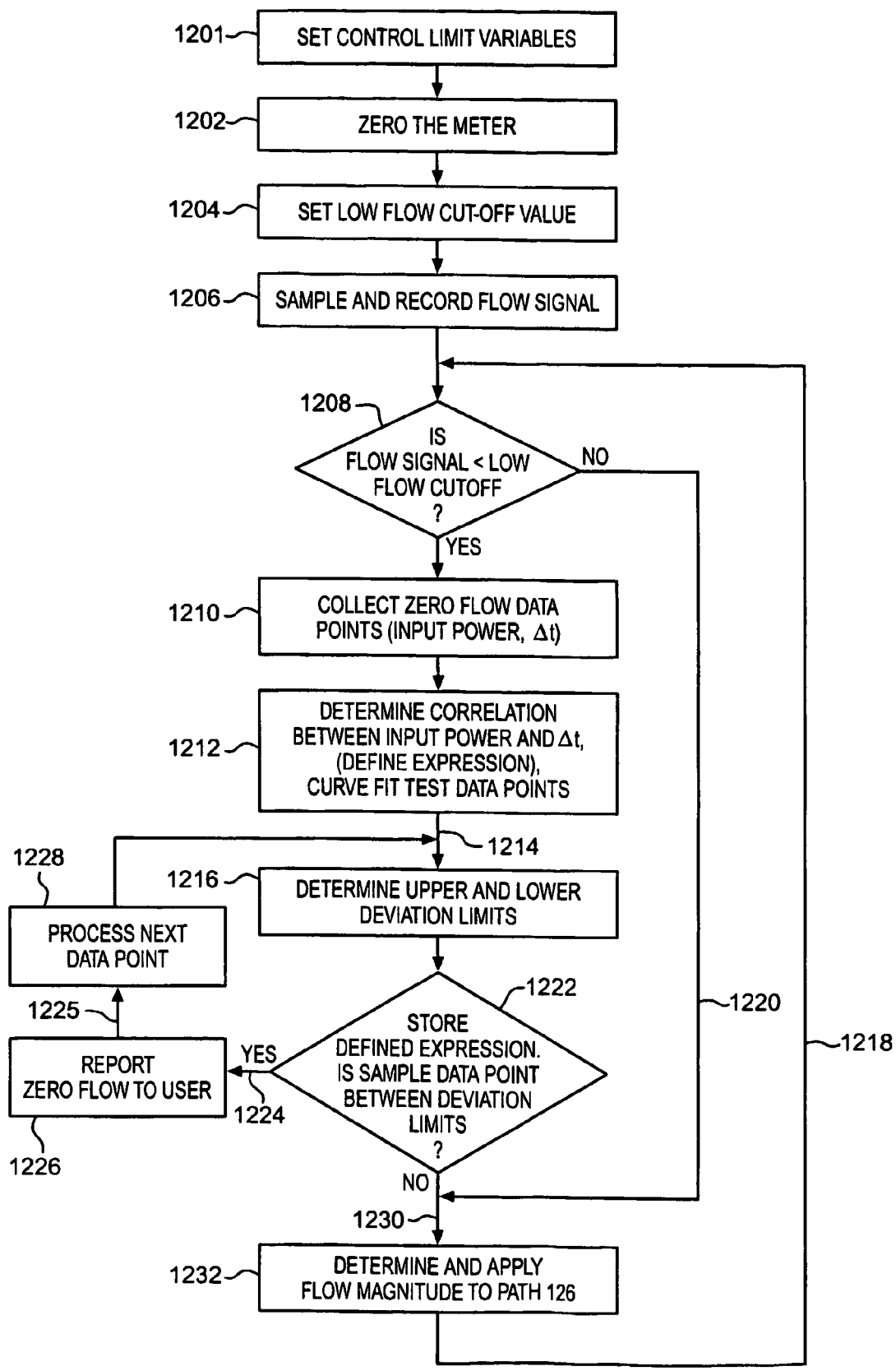
FIG. 12 a block diagram illustrating the process steps of the present invention.

Description of FIG. 12 The method and apparatus of the present invention prevents the application of erroneous flow information to path 126 during the zero flow state of the flowmeter. It does this by tracking the relationship of the input power to the $\Delta t$ detected by pickoffs 105 and 105' during the zero flow state. At the same time, adaptively changing deviation limits 804 and 805 that track the derived relationship between the input power and time delay Δt as samples 801 are created. Since the input power is indicative of the time delay, the time delay Δt between the pickoffs during the zero flow state is determined. The sampling of the input power signal is used to create data points that are curve fitted into an expression in the form of y=mx+b. On FIG. 8 this expression is used as a reference together with the subsequently sampled input power data points. During the sampling of each data point, a determination is made as to whether the amplitude of the sample is proximate the derived curve fitted expression 801 representing the relationship between the input power and time delay Δt. It is also determined at this time whether each sample is between the deviation limits 804 and 805 specified by the user. As long as the sampled data points remain within the deviation limits, the apparatus and method of the present invention causes the meter electronics 120 of FIG. 1 to report a zero as an output flow signal to the user on path 126.

The zero flow state terminates when a data point is sampled whose amplitude is either above the upper deviation limit 804 or below the lower deviation limit 805. The flowmeter is then determined to be in a true material flow state. At that time, the sampling of data points representing the curve fitted input power signal is terminated and meter electronics 120 uses the time delay signals generated by the pickoffs to apply a signal to path 126 representing the true material flow. This output signal 136 indicates the material flow under conditions in which the flow remains constant as well as under conditions in which the flow magnitude varies. This true material flow state continues until the magnitude of the flow falls below that of the user specified low flow cutoff valve. At that time, the flowmeter stops reporting a signal representing a true material flow and reverts to its zero flow state operation in which signals indicating the input power are sampled, curve fitted and used as described to apply a zero to the flowmeter output 126 representing the new zero flow state.

FIG. 12 illustrates one possible exemplary method by which the flowmeter apparatus is controlled to perform the above described functions. Element 701 sets the flowmeter control limit variables. These may include the variables associated with the horizontal and vertical axis of the graphs of FIGS. 6–11. Step 1202 zeros the flowmeter to determine the inherent time delay Δt between pickoffs 105 and 105' for a true zero flow condition. This compensates for any meter nonlinearities. Step 1204 sets the low flow cut-off value. Step 1206 collects and samples the time delay Δt the input power and converts these parameters into data points as described for FIGS. 10 and 11.

Step 1208 receives each sampled data point and determines whether it is less than the low flow cutoff value which is shown as "5" in the present description. If the sampled data point is not less than the low flow cutoff, a "No" signal is applied over paths 1220 and 1230 to element 1232 which determines and reports the flow magnitude represented by the sampled data point to output path 126 on FIG. 1.

The process loops back from element 1232 over path 1218 back to the input of element 708 which then receives the next data point from element 1206 and processes it as above described.

If the sampled data point received by element 1208 is below the low flow cut-off value, a "yes" signal is applied by element 1208 to the input of element 1210 which proceeds to collect a plurality of the zero flow data points representing input power and time delay Δt. Elements 1206 and 1208 may operate in this manner so that element 710 receives and temporarily stores a plurality of such data points representing a flow magnitude less than the value of the low flow cut-off specified by element 708. For example, element 1210 may collect approximately 20 data points over a time duration of approximately one second. The plurality of such data point received by element 1212 must be sufficient to permit element 1212, as next described, to perform its function of curve fitting the data points received by element 1212 into an expression representing the correlation between input power and time delay Δt as shown on FIG. 4.

Element 1212 determines when it has received a sufficient number of data points from element 1210 to perform a curve fitting function. In so doing, element 1212 determines the correlation between the input power and time delay Δt of the received plurality of data points and when it has received a sufficient plurality (20 or so) of data points from element 710, it performs a curve fitting operation to convert the data points into an expression of the form represented by y=mx+b where m is the slope of the defined expression and b is the y intercept of the defined expression. The defined expression is then applied from element 1212 over path 1214 to element 1216 which functions to determine the upper and lower deviation limits associated with the defined expression. These deviation limits are user determined and may be expressed in terms of percentile deviation from the derived expression or may be expressed in terms of probability. FIG. 8 shows a defined expression as well as an upper deviation limit 804 and a lower deviation limit 805.

Next, the output of element 1216 is applied to the input of element 1222 which stores the defined expression as well as the upper and lower deviation limits associated with the defined expression.

Element 1222 next receives subsequently sampled data points and of the input powers and determine each subsequently received data point is between the defined deviation limits 804 and 805. If element 1222 determines that a sampled data point is between the deviation limits, a "yes" signal is applied over path 1224 to element 1226 which causes meter electronics 120 to apply a zero as a flow signal to output path 126.

The process then extends over path 1225 to element 1228 which causes the next sampled data point to be received by element 1216 over path 1214. Element 1216 then performs the above indicated functions of determining the upper and lower deviation limits for the next sampled data point and applying this information to element 1222. Element 1222 then determines whether the newly sampled data point is within the deviation limits and applies a "yes" signal to path 1224 if the deviation is within limits or applies a "no" signal to path 1230 if the deviation is not within the deviation limits. The "yes" signal from element 1222 is processed as before described and loops from element 1226 and element 1228 and back to element 1216. The yes loop functions in this manner so long as a received sampled data point is within the deviation limits.

When a sampled data point is determined by element 1222 to be outside of the deviation limits, a "no" signal is generated and applied over path 1230 to element 1232 which determines that the zero flow state has ended and reports the magnitude of the flow represented by the newly received data point to path 126 of meter electronics 120. Element 1232 also applies a signal over path 1218 extending back to the input of element 1208. Since the flowmeter is now in a condition representing a true material flow, element 1208 receives the sample data point, and determines that it is not less than the low flow cut-off and applies a signal over "no" path 1220 and 1230 to element 1232 which continues to report the flow magnitude to path 126 and to extend a signal over path 1218 looping back to the input of element 1208.

The method of FIG. 12, continues to report a true material flow for each received data point until such time as element 1208 receives a sampled data point that is less than the low value of the low flow cut-off. The system then reverts to the zero flow state and functions as above described to cause a signal of zero to be extended from element 135 on FIG. 1 through contacts of switch 139 to output path 126 which reports a zero to the user for the duration of the zero flow state.

Figure 13:
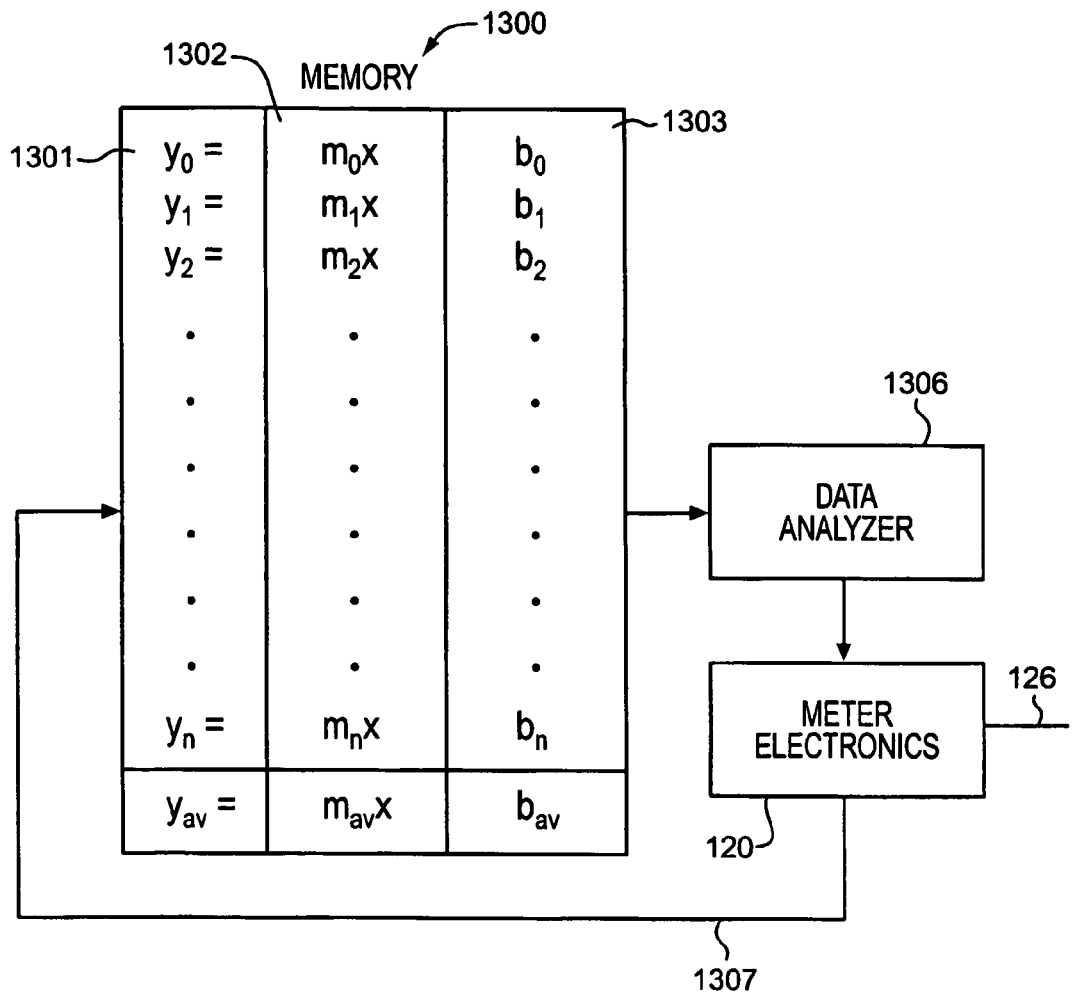
FIG. 13 discloses an embodiment of the invention that provides for the storing and of a plurality of derived expressions to enhance the performance of a Coriolis flowmeter embodying the invention.

Description of FIG. 13

FIG. 12 illustrates how the flowmeter of the present invention alternates between a zero flow state and a state of true material flow. It is further described on FIG. 12 how the beginning of each material flow state is characterized by a signal applied to element 1208 which indicates that the sample is below the low flow cut off value. Element 1208 then causes element 1212 to perform a curve fitting operation in which the first twenty or so of the data points of the newly initiated zero flow state are curve fitted to derive an expression representing the correlation between material flow, time delay and the input power to the flowmeter. It is also been described in connection with FIG. 12 how each derived expression is used to analyze the remainder of the data points of the same zero flow state during which the expression was derived.

FIG. 13 describes an embodiment of the invention in which the expressions derived during each zero flow state are stored in locations of memory 1300 having columns 1301, 1302, and 1309 for storing the various portions of each derived expression.

The first derived expression is $y_0=m_0x+b_0$ is stored in the first memory location. The successively derived expressions for the next plurality of zero flow states are stored in the successive locations of memory 800. The last expression is defined as $y_n=m_nx+b_n$.

Memory 1300 receives information from meter electronics 120 over path 1307 with each received entry being steered to the appropriate section of memory 800. The memory may be of the rotating type in which the first derived entries are stored in the indicated locations with subsequent entries being stored in the memory in a circular manner beginning with the first memory location. The memory is therefore always full and a newly derived expression is stored in the memory by writing it into a vacant location of memory, if empty, or by writing in to a next successive location by overwriting an existing entry. In this manner, memory 1300 is always full after the first "n" expressions have been received. Data analyzer 1306 analyzes the stored expressions, calculates the average of each parameters and stores the average in the bottom location by writing an expression $y_{av}=m_{av}x+b_{av}$. In so doing, the bottom location of the memory stores the average of the last "n" expressions.

In operation, it is desired that the various expressions should have consistent values for the variables of the slope m and the intercept b. An expression containing values for slope m and intercept b that differ greatly from the other expressions may indicate a trouble condition for which the flowmeter output should not be used. The data analyzer 1306 performs these functions and advises the meter electronics 120 of an inconsistency between a newly received expression and other expressions stored in the memory.

Figure 14:
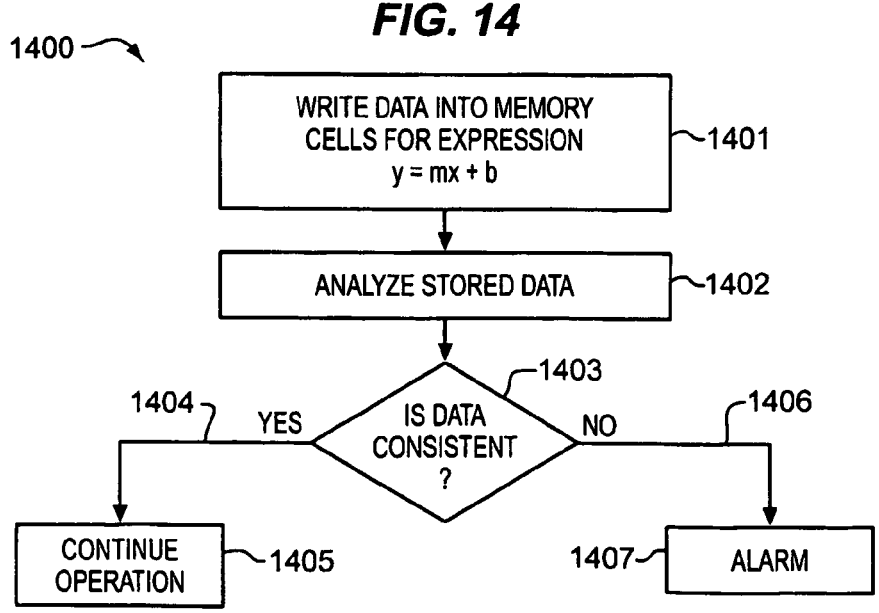
FIG. 14 is a flow chart illustrating the steps performed by the system of FIG. 13.

Description of FIG. 14

FIG. 14 discloses method steps performed by the system of FIG. 13 when an expression is received. Element 1401 receives the expression and writes it into the next available location memory 1300. Element 1402 reads the newly received expression and applies it to data analyzer 1406. Data analyzer 1406 analyzes the stored data for consistency between other data entries in memory 300 which represent the derived expressions for successive samples.

Element 1402 applies information pertaining to its data analysis to element 1403 which applies a signal to "yes" path 1404 if the data is consistent and does not contain abnormalities. If the data is inconsistent or contains abnormalities it should be further investigated, a signal is applied to "no" path 1406. The application of a signal to "yes" path 904 causes the system to continue normal system operation. This would include the analysis of additional entries as they are written into memory 1300. The application of a "no" signal to path 1406 can initiate a system alarm 1407 or, if desired, can shut down the system by terminating material flow.

Figure 15:
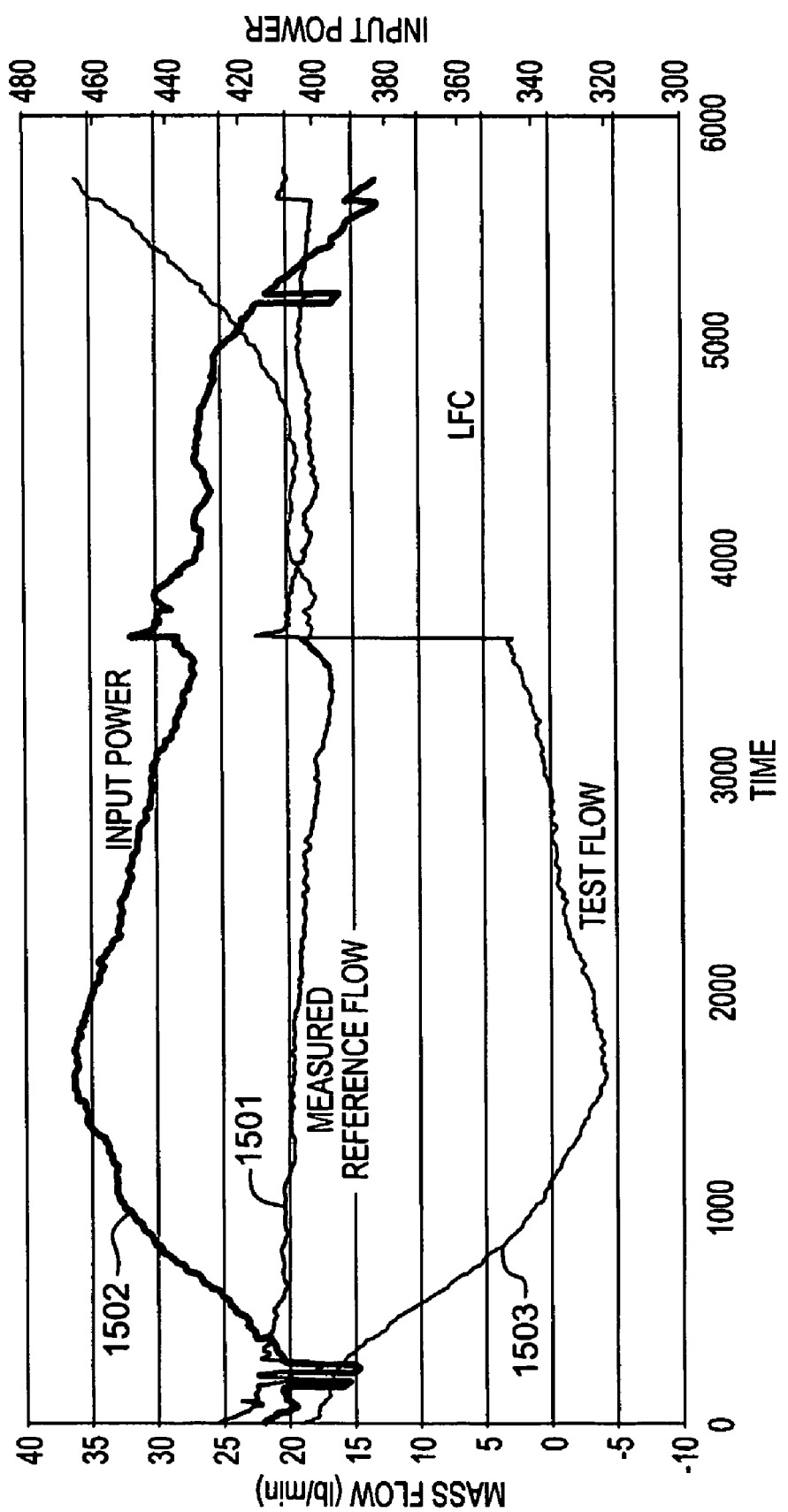
FIG. 15 shows the parameter variations for a flowmeter embodying the invention during a state of low material flow.
Figure 16:
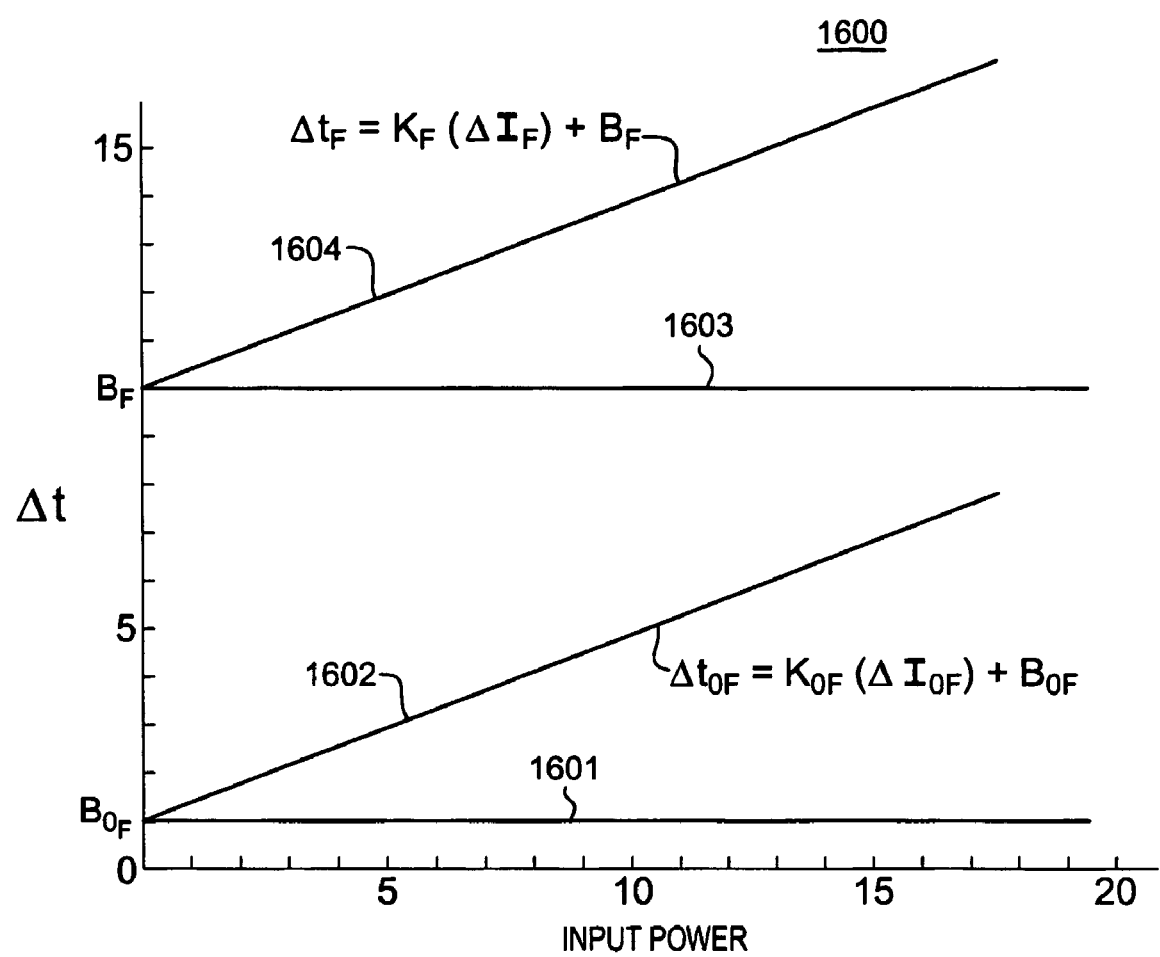
FIG. 16 illustrated the expressions used in compensating output information of low flow states.
Figure 17:
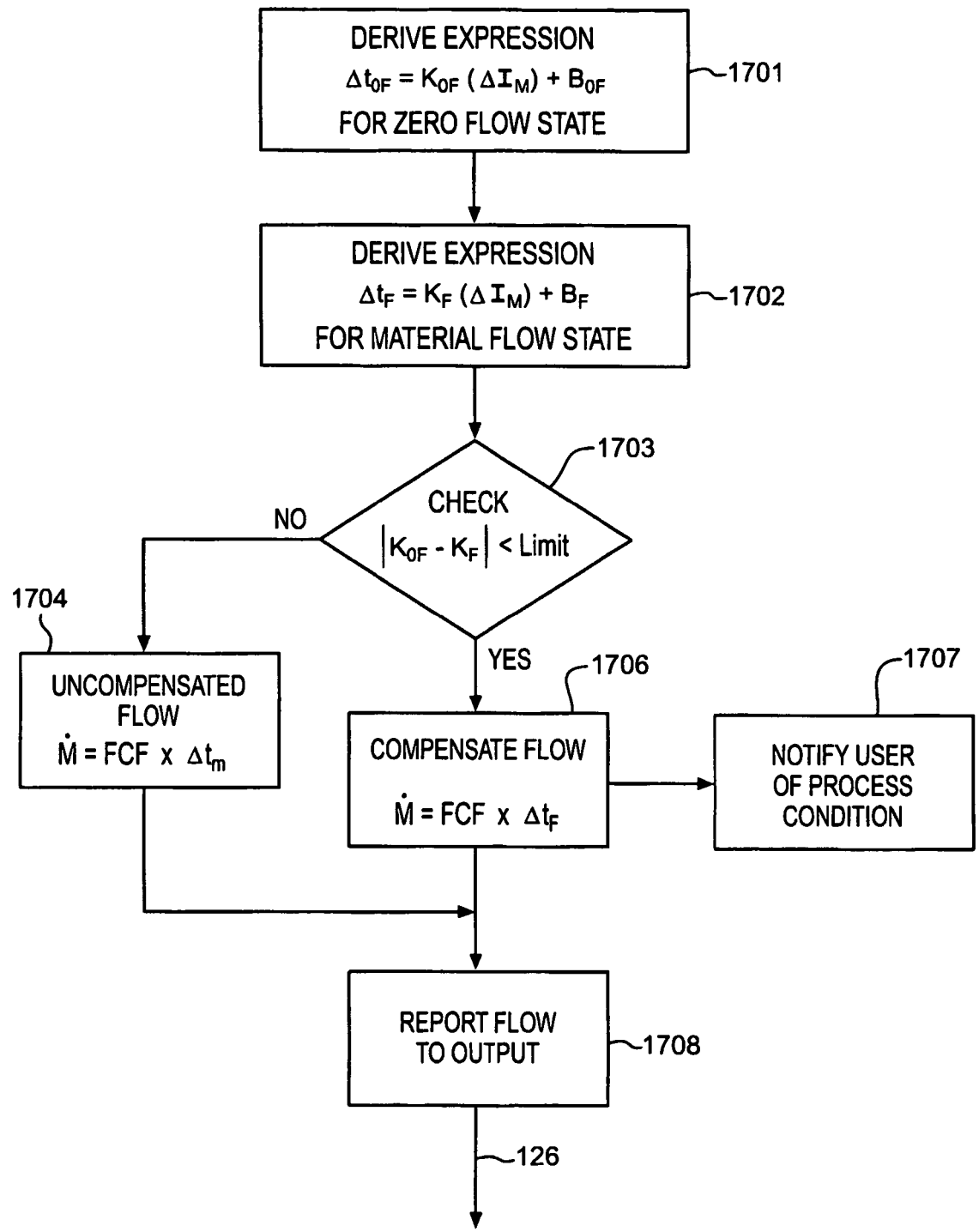
FIG. 17 illustrates the processing steps that may be utilized during the samples of flow signals to improve the accuracy of the output signals generated by a flowmeter during a condition of low material flow.

Description of Another Possible Embodiment—
FIGS. 15–17

Description of FIG. 15

The preceding has described how a Coriolis flowmeter system embodying the present invention prevents the generation of spurious flowmeter signals to path 126 during a zero flow state during which there is no flow through the flowmeter. In accordance with the method and apparatus embodying the invention, the zero flow state is detected, a source of zero potential 135 is applied to output 126 for the duration of the zero flow state, the zero flow correction element 133 and the flow information generator 132 together function to analyze the time delay signals between the pickoffs 105 and 105'. The spurious time delay signals are monitored until the magnitude of the flow signals they represent exceed a deviation limit indicative of a true material flow. At such times, the zero flow correction circuitry 133 and the flow information generator 132 then together function to terminate the sampling of the zero flow state and apply an output signal to path 126 representing a true material flow.

The same material abnormalities that are responsible for the generation of spurious signals during the zero flow state may also be present in the material flow during conditions of low material flow. They can cause errors in the output information generated by the flowmeter during the low flow conditions. This is shown on FIG. 15 which illustrates characteristics of a flowmeter during conditions of a relatively low amplitude material flow rate. The illustrated parameters on FIG. 15 are measured with a reference flowmeter in series with the flowmeter under tests. The reference measured flow is shown as path 1501 on FIG. 15. It is relatively constant in magnitude from time "0" to approximately time 5000. The output signal generated by the meter under test is shown as path 1503 and various considerably from time "0" until approximately time 3700. At time 3700, the meter was reset to zero and recalibrated and from then on the test flow remained relatively constant at a level of 18.

FIG. 15 shows path 1502 representing the variation in input power during the test run associated with path 1503. Input power 1502 begins approximately at time "0" and increases to a maximum at time 1500 following which it decreases until time 3700 when the meter was reset.

The variations in test flow 1503 are opposite and symmetrical with the increases input power 1502 over the duration of the test. Since the measured reference flow 1501 is relatively constant during this test interval, the variations in the test flow 1003 together with the variations in input power 1502 are due to the same material abnormalities that cause the generation of spurious signals for time delay during the previously described zero flow state of the flowmeter.

FIG. 15 shows that these errors are significant during the low flow state of the flowmeter. Thus, at time 1500, the test flow 1503 is shown as a "−4" while the input power 1503 is a maximum slightly above level 460. Since the measured reference flow 1501 remain constant at a flow rate of approximately 20 during the tests, it can be seen that errors generated by these material abnormalities and generated spurious signals indicate that the test flow was −4 rather than a positive flow rate of 20 as shown by the measured reference flow 1501. Thus, test flow 1503 was rendered unreliable by the abnormalities in the material and the spurious signals that generated so as to render information generated by the flowmeter at this time unreliable.

FIG. 7 shows the variation in input power represents a corresponding variation in the Δt which, in turn, represents a variation in the indicated flow rate. In other words, the variation on input power on FIG. 15 for line 1502 is directly related to variations in time delay Δt as shown on FIG. 7 which in turn is related to the mass flow rate as shown on FIG. 15. Since the input power 1502 varies during the duration of the test flow, it must be assumed that the variation in input power 1502 and the corresponding variation in test flow 1503 is due to the material abnormalities previously discussed and spurious time delay signals these abnormalities generate during a zero flow state. The same abnormalities and spurious signals are present in the information generated by the flowmeter during conditions of low magnitude material flow.

Description of FIG. 16

In accordance with yet another possible exemplary embodiment of the invention, the problems associated with presence of material abnormalities and spurious time delay signals at low levels of material flow are eliminated by first deriving an expression as priorly described for the input power associated with the spurious time delay signals during a zero flow state. Such an expression is shown as path 1602 on FIG. 16 where the derived expression is $$\Delta t_{0F} = K_{0F}(DI_{0F}) + B_{0F}$$

This expression has an intercept on the y axis at location $B_{0F}$ and has a slope of $K_{0F}$. Next, the same flowmeter containing the same material is operated during a condition of low flow. A curve fitted expression is then derived for this low flow state of the flowmeter. The expression is shown for path 1604 and is $$\Delta t_F = K_F(DI_F) + B_F.$$

The slope of equation 1604 is $K_F$ while the intercept on the Δt axis is $B_F$. The slope of equations 1602 and 1604 are identical so that $K_F$ must be equal to $K_{0F}$.

For the expression of line 1602, the distance between any location on line 1602 and the horizontal line 1601, also termed $B_{0F}$, is due to the spurious signals generated by the flowmeter during a zero flow state. The angle between line 1602 and line 1601 is equal to the angle between lines 1604 and 1603. It is therefore obvious that the distance between any point on line 1604 and line 1603 is similarly due to the spurious signals generated by abnormalities in the material flow due to bubbles and the like. This being the case, the magnitude of the true material flow for line 1603 is determined by the distance between the y intercept $B_F$ for a low flow magnitude and the y axis intercept $B_{0F}$ for the zero flow state of the flowmeter. The expressions shown on FIG. 11 and the interrelationships there between are used in calculating the true material flow are shown on FIG. 17.

Description of FIG. 17

FIG. 17 describes the method steps used to derive a corrected material flow for the magnitude of material flow portrayed by the graphs of FIG. 16.

The process 1700 begins with element 1701 which derives the expression $$\Delta t_{0F} = K_{0F}(\Delta I_M) + B_{0F}$$

This expression is for the zero flow state of the flowmeter. Next, element 1702 derives a curve fitted expression $\Delta t_F$ for the low material flow state shown on line 1604. Next, element 1703 solves the expression embodying the terms $\Delta t_f$ and $\Delta t_0$ and the relevant limits. Element 1204 then solves the expressions $$\dot{M} = FCF \times \Delta t_m$$

$$\dot{M} = FCF \times \Delta t_F$$

Elements 1703 checks the value of $K_{0F} - K_F$ against user specified limits. If the limits are not met, element 1703 applies a "No" signal to element 1704 which reports an uncompensated flow rate to element 1708 and path 126. If the limits are met, element 1703 applies a "Yes" signal to element 1706 which reports a compensated flow rate $\dot{M}$ to element 1708 and path 126 and also notifies a user in element 1707 of the process condition. The limit used by element 1703 may, if desired, be the term $y_{av} = m_{av}x + b_{av}$ stored in memory 1300.

The method of FIG. 17 derives a corrected value for the low flow state of the flowmeter by eliminating the effects of the material abnormalities and the spurious signals they generate.

It is to be expressly understood that the claimed invention is not to be limited to the description of the preferred embodiment but encompasses other modifications and alterations. For example, although the present invention has been disclosed as comprising a part of a single straight or dual tube flowmeter, it is to be understood that the present invention is not so limited and may be used with other types of flowmeters including single tube flowmeters of irregular or curved configuration as well as flowmeters having a plurality of flow tubes. Also the method and apparatus of the present invention can be used with other types of flow measurement devices in addition to a Coriolis flowmeter.

What is claimed is:

1. Meter electronics (120) for a flow measurement apparatus having a processing system for correcting flow information generated by said flow measurement apparatus; said meter electronics (120) comprising:
   instructions for directing said processing system to:
   sample a signal representing flow information generated by said flow measurement apparatus during a zero flow state of said flow measurement apparatus to define a plurality of data points representing said signal;
   establish deviation limits for at least one of said data points;

determine whether each sampled data point is within said deviation limits;

sample a data point within said deviation limits to define spurious flow information for said zero flow state;

sample a data point outside of said deviation limits to define information representing a true material flow of said flow measurement apparatus;

continue said sampling of said data points as long as said sampled data points are within said deviation limits;

prevent said spurious flow information from being applied as to an output of said flow measurement apparatus during the sampling of data points within deviation limits;

determine that the most recently sampled data point is outside of said deviation limits and thereby represents information for a true material flow of said flow measurement apparatus; and generate an output signal representing said true material flow information represented by said most recently sampled data point.

2. The meter electronics (120) of claim 1 characterized in that said flow measurement apparatus defines a Coriolis flowmeter.

3. The meter electronics (120) of claim 1 characterized in that said processing system is configured to execute the further instructions of:

specify a low flow cutoff limit representing a material flow below which said flow measurement apparatus will not generate an output signal representing a true material flow;

monitor the material flow information represented by said output signal;

determine that said monitored material flow information becomes less than the material flow represented by said low flow cutoff limit;

terminate the generation of said output signal; and resume the sampling of the said data points for said zero flow state of said flow measurement apparatus.

4. The meter electronics (120) of claim 3 characterized in that said processing system is configured to execute the further instructions of:

determine that a newly sampled data point represents a material flow that is outside of said deviation limits; and generate an output signal for the true material flow represented by said newly sampled data point.

5. The meter electronics (120) of claim 1 characterized in that said processing system is configured to execute the further instructions of:

determine the average p of the flow rates of the N previously sampled data points;

establish said standard deviation limits of the previous N data points by multiplying the product of the standard deviation r by a user specified number standard deviations A away from said average of the deviations; and add and subtract the product of rA with respect to μ.

6. The meter electronics (120) of claim 3 characterized in that said processing system is configured to execute the further instructions of:

use a relationship between time delay Δt and input power of said flow measurement apparatus to derive an expression representing a plurality of said data points characterizing the generation of flow information by said flow measurement apparatus during said zero flow state.

7. The meter electronics (120) of claim 6 characterized in that said processing system is configured to execute the further instructions of:

determine the deviation between subsequently sampled data points and said expression; and use said deviation determination to detect the end of said zero flow state.

8. The meter electronics (120) of claim 7 characterized in that said processing system is configured to execute the further instructions of:

derive a plurality of said expressions for said zero flow state;

store said plurality of derived expressions in a memory;

define consistency information;

compare a newly derived expression with said stored expressions;

determine whether said newly derived expression is consistent with said stored expressions;

use said newly defined expression if it is determined to be consistent with said stored expressions; and preclude the use of said newly defined expression if it is determined to be inconsistent with said stored expressions.

9. The meter electronics (120) of claim 6 characterized in that said processing system is configured to execute the further instructions of:

derive said expression by sampling said data points; and use "n" of said data points in a curve lifting operation to derive said expression.

10. The meter electronics (120) of claim 9 characterized in that said processing system is configured to execute the further instructions of:

sample the remainder "m" of said sampled data points;

determine the deviation between each of said "m" sampled data points and said expression; and use said deviation determination to determine the operational state of said flow measurement apparatus.

11. The meter electronics (120) of claim 1 characterized in that said processing system is configured to execute the further instructions of:

establish said deviation limits by the step of establishing an upper limit and a lower limit of deviation associated with each sampled data point;

sample said data points as long as the spurious material flow information represented by said data point is between said upper deviation limit and said lower deviation limit;

determine that a newly sampled data point falls outside of said limits;

determine the true material flow information represented by said sampled data point; and generate an output signal representing said determined flow information.

12. The meter electronics (120) of claim 1 characterized in that said processing system is configured to execute the further instructions of:

derive an expression to define data points characterizing the parameters of time delay Δt and input power of said flow measurement apparatus during a low flow state of said flow measurement apparatus;

derive an expression to define data points characterizing the parameters of Δt and input power of said flow measurement apparatus during a zero flow state of said flow measurement apparatus; and subtract said defined expression for said zero flow state from said expression for said low flow state to obtain an output signal for said flow measurement apparatus that is devoid of the spurious errors induced in said apparatus during said zero flow state.

13. Meter electronics (120) for a flow measurement apparatus having a processing system for correcting flow information generated by said flow measurement apparatus; said meter electronics (120) comprising:

instructions for directing said processing system to:

derive an expression to define data points for a signal characterizing the parameters of time delay $\Delta t$ and input power of said flow measurement apparatus during a zero flow state of said flow measurement apparatus;

derive an expression to define data points characterizing the parameters of time delay $\Delta t$ and input power of said flow measurement apparatus during a low flow state of said flow measurement apparatus;

subtract said expression for a zero flow state of said flow measurement apparatus from said expression for said low flow state to obtain an output signal devoid of the errors induced during said zero flow state.

14. A method of operating a flow measurement apparatus for correcting flow information generated by said flow measurement apparatus, said method comprising the steps of:

sampling a signal representing flow information generated by said flow measurement apparatus during a zero flow state of said flow measurement apparatus to define a plurality of data points representing said signal;

establishing deviation limits for at least some of said data points;

determining whether each sampled data point is within said deviation limits;

sampling a data point within said deviation limits to define spurious flow information for said zero flow state;

sampling a data point outside of said deviation limits to define information representing a true material flow of said flow measurement apparatus;

continuing said sampling of said data points as long as said sampled data points are within said deviation limits;

preventing said spurious flow information from being applied as to an output of said flow measurement apparatus during the sampling of data points within deviation limits;

determining that the most recently sampled data point is outside of said deviation limits and thereby represents information for a true material flow of said flow measurement apparatus; and generating an output signal representing said true material flow information represented by said most recently sampled data point.

* * * * *

UNITED STATES PATENT AND TRADEMARK OFFICE
CERTIFICATE OF CORRECTION

| | | |
|---|---|---|
| PATENT NO. | : 7,194,368 B2 | Page 1 of 1 |
| APPLICATION NO. | : 10/566613 | |
| DATED | : March 20, 2007 | |
| INVENTOR(S) | : Charles Paul Stack, Craig B. McAnally and Gregory Treat Lanham | |

It is certified that error appears in the above-identified patent and that said Letters Patent is hereby corrected as shown below:

Column 8, line 6, replace "at" with --$\Delta t$--.

Column 15, line 28, replace "to" with -- $t_9$ --; line 42, replace "flows" with --flow'--.

Column 20, line 40, replace "$\Delta t$" with --At--.

Column 23, line 51, replace "p" with --$\mu$--.

Column 24, line 28, replace "lifting" with --fitting--.

Signed and Sealed this

Twenty-seventh Day of November, 2007

JON W. DUDAS
*Director of the United States Patent and Trademark Office*